(12) United States Patent
Mulqueen et al.

(10) Patent No.: US 12,408,928 B2
(45) Date of Patent: Sep. 9, 2025

(54) SURGICAL INSTRUMENTS INCLUDING MARKING TOOLS AND CUT GUIDES

(71) Applicant: Zimmer Biomet Pty Ltd, Belrose (AU)

(72) Inventors: Marika Mulqueen, Strathdale (AU); Massoud Akbarshahi, Belrose (AU); Maximilian Pentecost, Belrose (AU)

(73) Assignee: Zimmer Biomet Pty Ltd, Belrose (AU)

( * ) Notice: Subject to any disclaimer, the term of this patent is extended or adjusted under 35 U.S.C. 154(b) by 462 days.

(21) Appl. No.: 17/684,828

(22) Filed: Mar. 2, 2022

(65) Prior Publication Data

US 2022/0287722 A1 Sep. 15, 2022

Related U.S. Application Data

(60) Provisional application No. 63/159,770, filed on Mar. 11, 2021.

(51) Int. Cl.
*A61B 17/15* (2006.01)

(52) U.S. Cl.
CPC ................ *A61B 17/15* (2013.01)

(58) Field of Classification Search
CPC .......... A61B 17/155–17/1668; A61B 34/10–2034/258
See application file for complete search history.

(56) References Cited

U.S. PATENT DOCUMENTS

| | | | |
|---|---|---|---|
| 4,959,066 A | 9/1990 | Dunn et al. | |
| 5,540,696 A * | 7/1996 | Booth, Jr. | A61B 17/025 606/88 |
| 6,258,097 B1 * | 7/2001 | Cook | A61F 2/4657 606/91 |
| 8,070,752 B2 * | 12/2011 | Metzger | G16H 20/40 606/88 |
| 8,092,465 B2 | 1/2012 | Metzger et al. | |
| 8,282,646 B2 | 10/2012 | Schoenfeld et al. | |

(Continued)

FOREIGN PATENT DOCUMENTS

| | | |
|---|---|---|
| EP | 1588668 | 10/2005 |
| EP | 3815630 | 5/2021 |

(Continued)

OTHER PUBLICATIONS

"European Application Serial No. 20204413.7, Extended European Search Report mailed Mar. 22, 2021", 7 pgs.
"Australian Application Serial No. 2020257132, First Examination Report mailed Jun. 29, 2021", 4 pgs.
"Australian Application Serial No. 2020257132, Response filed Aug. 20, 2021 First Examination Report mailed Jun. 29, 2021", 15 pgs.

(Continued)

*Primary Examiner* — Zade Coley
(74) *Attorney, Agent, or Firm* — SCHWEGMAN LUNDBERG & WOESSNER, P.A.

(57) ABSTRACT

Various orthopedic systems and techniques are disclosed. The systems according to one example can include a first portion configured to moveably couple to the first end of a body and configured to reference a first surface of the bone positioned to a first side of a longitudinal axis of the bone and a second portion configured to moveably couple to the second end of the body and configured to reference a second surface of the of the bone positioned to a second side of the longitudinal axis of the bone. Other orthopedic systems utilize an arm and a plurality shims. Each shim can be configured to couple with the arm and can reference a junction between a neck of the femur and a lesser trochanter of the femur.

17 Claims, 25 Drawing Sheets

(56) References Cited

U.S. PATENT DOCUMENTS

| | | | |
|---|---|---|---|
| 8,298,237 | B2 | 10/2012 | Schoenfeld et al. |
| 8,407,067 | B2 | 3/2013 | Uthgenannt et al. |
| 8,473,305 | B2 | 6/2013 | Belcher et al. |
| 8,568,487 | B2 | 10/2013 | Witt et al. |
| 9,241,745 | B2 | 1/2016 | Smith et al. |
| 9,345,548 | B2 | 5/2016 | Schoenefeld et al. |
| 9,907,659 | B2 | 3/2018 | Belcher et al. |
| 9,931,168 | B2 | 4/2018 | Brown |
| 11,642,137 | B2 | 5/2023 | Mulqueen et al. |
| 2004/0236341 | A1* | 11/2004 | Petersen ............... A61B 17/15 606/88 |
| 2005/0113839 | A1* | 5/2005 | Yoon ............... A61B 17/1659 606/85 |
| 2008/0257363 | A1 | 10/2008 | Schoenefeld et al. |
| 2014/0276866 | A1* | 9/2014 | Endsley ............... A61F 2/4657 606/89 |
| 2016/0374697 | A1 | 12/2016 | Kehres et al. |
| 2018/0177611 | A1* | 6/2018 | Trabish ............... A61B 17/1626 |
| 2018/0296232 | A1* | 10/2018 | Nielsen ............... A61B 17/155 |
| 2021/0121184 | A1* | 4/2021 | Mulqueen ............... A61B 34/10 |
| 2021/0236145 | A1 | 8/2021 | Beverland |
| 2021/0259705 | A1 | 8/2021 | Beverland et al. |

FOREIGN PATENT DOCUMENTS

| | | |
|---|---|---|
| WO | 2010129870 | 11/2010 |
| WO | 2020001830 | 1/2020 |
| WO | 2020002190 | 1/2020 |

OTHER PUBLICATIONS

"Australian Application Serial No. 2020257132, Subsequent Examiners Report mailed Sep. 16, 2021", 6 pgs.

"European Application Serial No. 20204413.7, Response filed Nov. 5, 2021 to Extended European Search Report mailed Mar. 22, 2021", 17 pgs.

"Australian Application Serial No. 2020257132, Response filed Nov. 11, 2021 to Subsequent Examiners Report mailed Sep. 16, 2021", 11 pgs.

"Australian Application Serial No. 2020257132, Subsequent Examiners Report mailed Nov. 25, 2021", 3 pgs.

"Australian Application Serial No. 2020257132, Response filed Jan. 24, 2022 to Subsequent Examiners Report mailed Nov. 25, 2021", 8 pgs.

Lustig, Sebastien, "Step by Step Guide How to template the Hip", [Viewed on internet on Nov. 22, 2021] Viewed on internet. URL: http: orthopedie-lyon.fr wp-content uploads 2016 12 template-the-hip-min.pdf, (2016), 25 pages.

"U.S. Appl. No. 17/079,019, Restriction Requirement mailed May 26, 2022", 8 pgs.

"U.S. Appl. No. 17/079,019, Response filed Jul. 20, 2022 to Restriction Requirement mailed May 26, 2022", 8 pgs.

"U.S. Appl. No. 17/079,019, Non Final Office Action mailed Sep. 2, 2022", 20 pgs.

"U.S. Appl. No. 17/079,019, Response filed Nov. 28, 2022 to Non Final Office Action mailed Sep. 2, 2022", 17 pgs.

"U.S. Appl. No. 17/079,019, Notice of Allowance mailed Jan. 3, 2023", 10 pgs.

* cited by examiner

SURGICAL INSTRUMENTS INCLUDING MARKING TOOLS AND CUT GUIDES

CLAIM OF PRIORITY

This application claims the benefit of U.S. Provisional Patent Application Ser. No. 63/159,770, filed on Mar. 11, 2021, the benefit of priority of which is claimed hereby, and which is incorporated by reference herein in its entirety.

FIELD

The present subject matter relates to surgical apparatuses, systems and methods, and more particularly, to surgical apparatuses and related systems and methods that allow a bone cut to made with a desired location and orientation.

BACKGROUND

Resection or cut guides are used in various orthopedic surgical procedures including in a total femoral hip arthroplasty. Part of this procedure removes a damaged head of the femur with the guide aiding such removal by guiding the cut(s) (also termed resection(s)) performed by a surgeon. Prosthetic devices recreating the hip joint are then implanted on the remaining bone of the femur and in bone of the patient's hip.

OVERVIEW

This disclosure pertains generally to apparatuses, systems and methods that help overcome challenges that can arise during orthopedic surgery. One such challenge can be properly locating a cut guide or resection considering a patient's anatomy (e.g., bone size, shape and orientation). This anatomy varies from patient to patient. It can be time consuming and sometime complicated for the surgeon to make appropriate anatomical measurements, adjust instruments such as the cut guide according to such measurements and locate the cut guide properly and perform other tasks related to the orthopedic surgery.

The present inventors have recognized, among other things, positioning apparatuses (also commonly called an alignment guides) that facilitate a desired positioning for a resection that can take into account a patient's individual anatomy. Such positioning apparatuses are configured to reduce surgical time and complexity as they are intuitive to use and have reduced complexity as compared with traditional alignment and cut guides.

Although described in reference to a femur, the apparatuses, systems and methods of the present application are applicable to other bones or bone portions including the humerus and distal femur.

According to one aspect this application, the present inventors have recognized, among other things, orthopedic alignment and cut guides can benefit from virtual surgery planning systems and methods. Such systems and methods can facilitate the virtual identification of bone that should be removed and can virtually identify a shape, angle, and/or length of bone portions to be removed. The systems and methods can additionally facilitate the selection of appropriate settings for positioning a cut guide with one or more alignment guides such that the cut guide has a patient-appropriate size and/or angle of cut. Using the virtual surgery planning systems and methods, procedures such as resection of the neck of a femur below the femoral head can be simplified so as to be performed more rapidly, with a lesser number of measurements having to be performed by the surgeon, and in a more reproducible surgical manner. Thus, the present inventors have invented, apparatuses systems and methods that include an adjustable cut guide and adjusting settings on the cut guide based on anatomy of the patient. In some cases, the techniques discussed can be used in combination with output from a visualization system to modify the position of the cut guide to be specific to an individual patient's anatomy.

To further illustrate the apparatuses, systems and methods disclosed herein, the following non-limiting examples are provided:

Example 1 is an orthopedic system that can optionally include a body, a first portion and a second portion. The body can have a longitudinal extent, with a first end opposing a second end. The body can be configured to extend across an end portion of a bone. The first portion can be configured to moveably couple to the first end of the body and can be configured to reference a first surface of the bone positioned to a first side of a longitudinal axis of the bone. The second portion can be configured to moveably couple to the second end of the body and can be configured to reference a second surface of the of the bone positioned to a second side of the longitudinal axis of the bone.

Example 2 is the system of Example 1, wherein optionally the body can have a surface for guiding a resection of the end portion of the bone.

Example 3 is the system of any one of Examples 1-2, wherein optionally the first portion can be configured to reference a proximal surface of a greater trochanter of a femur and the second portion can be configured to reference a junction between a neck of the femur and a lesser trochanter of the femur.

Example 4 is the system of any one of Examples 1-3, wherein optionally the first portion can have a first linear track having a first plurality of teeth that engage mating teeth of a first actuator, and wherein the second portion can have a second linear track having a second plurality teeth that engage mating teeth of a second actuator.

Example 5 is the system of any one of Examples 1-4, wherein optionally the body includes a first spring biased finger configured to engage a one of a linear arrangement of a first plurality of detents to lock the first portion in position relative to the body, and wherein optionally the body includes a second spring biased finger configured to engage a second one of a linear arrangement of a second plurality of detents to lock the second portion in position relative to the body.

Example 6 is the system of any one of Examples 1-5, wherein optionally the body and the first portion each have first indicia, the first indicia can be indicative of a distance between a greater trochanter and a proximal surface of the body, and wherein optionally the body and the second portion each have second indicia, the second indicia can be indicative of a distance between the a junction between a neck of the femur and a lesser trochanter of the femur and the proximal surface of the body.

Example 7 is the system of any one of Examples 1-5, optionally further comprising: a computer including at least one processor and a memory device, the memory device including instructions that, when executed by the at least one processor, cause the computer to: access image data of a target location including the bone of a patient, the image data including at least one of a bone size, a bone orientation and a bone shape; display based upon the collected image data one or more patient-specific characteristics of bone; determine one or more of a size, a shape and an orientation for an osteotomy of the end portion of the bone based at least in part upon the one or more patient-specific characteristics of the bone; and convert the one or more patient-specific characteristics of the anatomy of the patient to a first setting to position the first guide portion relative to the body and a second setting to position the second guide portion relative to the body.

Example 8 is the system of Example 7, optionally further comprising instructions that cause the computer to construct a virtual model of the bone, wherein the virtual model displays a virtual rendering of the body, the first portion and the second portion and approximates the positioning the first portion, the body and the second portion relative to the bone along with the one or more patient-specific characteristics of the bone of the patient.

Example 9 is the system of any one of Examples 7-8, wherein optionally the first setting and the second setting can be one of a plurality of standard settings for the first portion and the second portion, and the first setting and the second setting can be selected as a best match to the one or more patient-specific characteristics of the bone, and wherein the first portion, the second portion and the body can have indicia corresponding to the plurality of standard settings, including first indicia indicative of a distance between a greater trochanter and a proximal surface of the body and second indicia can be indicative of a distance between the a junction between a neck of the femur and a lesser trochanter of the femur and the proximal surface of the body.

Example 10 is an orthopedic system optionally comprising an assembly and a plurality of shims. The assembly can include a handle and an arm projecting from the handle. The plurality shims can include that each shim can be configured to couple with the arm. The plurality of shims can each be of a different thickness and can be configured to reference a junction between a neck of the femur and a lesser trochanter of the femur. When one of the plurality of shims is coupled to the arm and positioned to reference the junction, the one of the plurality of shims can position a proximal surface of the arm a predetermined distance from the junction.

Example 11 is the orthopedic system of Example 10, wherein optionally one or more of the plurality of shims can have a longitudinal length, and wherein optionally a first end portion along the longitudinal length has a first thickness and a second end portion along the longitudinal length opposing the first end portion has a second thickness, and wherein the first thickness differs from the second thickness.

Example 12 is the orthopedic system of Example 11, wherein optionally each shim of the plurality of shims has two connection features to couple to the arm.

Example 13 is the orthopedic system of any one of Examples 10-12, wherein optionally the proximal surface of the arm can be configured to guide marking of the femur from a first side of a longitudinal axis of the femur adjacent the junction across the femur to a second side of the longitudinal axis at or adjacent a greater trochanter.

Example 14 is the orthopedic system of any one of Examples 10-13, wherein optionally the handle can have indicia therein for alignment of the assembly with a longitudinal axis of the femur.

Example 15 is the orthopedic system of any one of Examples 10-14, optionally further comprising: a computer including at least one processor and a memory device, the memory device including instructions that, when executed by the at least one processor, cause the computer to: access image data of a target location including the femur of a patient, the image data including at least one of a femur size, a femur orientation and a femur shape; display based upon the collected image data one or more patient-specific characteristics of the femur; determine one or more of a size, a shape and an orientation for an osteotomy of a proximal end of the bone based at least in part upon the one or more patient-specific characteristics of the femur; and convert the one or more patient-specific characteristics of the anatomy of the patient to a indicate a desired one of the plurality of shims according to a pre-operative plan.

Example 16 is the system of Example 15, optionally further comprising instructions that cause the computer to construct a virtual model of the femur, wherein the virtual model displays a virtual rendering of the orthopedic system and approximates the positioning the assembly and the one of the plurality of shims relative to the femur along with the one or more patient-specific characteristics of the femur of the patient.

Example 17 is an orthopedic system optionally comprising an assembly and a body. The assembly can include a first arm and a second arm, wherein the first arm can be configured to rest against a saddle of a neck of a femur. The body can be configured to couple with the assembly. The body can include a moveable portion configured to retract and extend relative to the assembly. The body can include a plurality of indicia configured to indicate a distance between the first arm and a distal end of the body.

Example 18 is the orthopedic system of Example 17, wherein the movable portion of the body can be retractable and extendable to indicate a depth of a proximal surface of a broach when the broach is inserted in the femur according to a pre-operative plan.

Example 19 is the orthopedic system of any one of Examples 17-18, wherein the body can include a stationary bolt that resides within the moveable portion.

Example 20 is the orthopedic system of any one of Examples 17-19, wherein the distal end of the body can be flared to engage a surface of the femur, wherein the distal end of the body can be configured to guide marking of the surface of the femur.

Example 21 is the orthopedic system of any one of Examples 17-20, optionally further comprising: a computer including at least one processor and a memory device, the memory device including instructions that, when executed by the at least one processor, cause the computer to: access image data of a target location including the femur of a patient, the image data including at least one of a femur size, a femur orientation and a femur shape; display based upon the collected image data one or more patient-specific characteristics of the femur; determine one or more of a size, a shape and an orientation for an osteotomy of a proximal end of the bone based at least in part upon the one or more patient-specific characteristics of the femur; and convert the one or more patient-specific characteristics of the anatomy of the patient to a setting to position the moveable portion of the body relative to the first arm to approximate a proximal surface of a broach when the broach is inserted in the femur according to a preoperative plan.

Example 22 is the system of Example 21, optionally further comprising instructions that cause the computer to construct a virtual model of the femur, wherein the virtual model displays a virtual rendering of the orthopedic system and approximates the positioning the assembly and the moveable portion relative to the femur along with the one or more patient-specific characteristics of the femur of the patient.

The foregoing Examples can be combined or features of any Example thereof can be selected in any manner as would be contemplated by one of ordinary skill in the art in view of this disclosure.

These and other examples and features of the present apparatuses, systems and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses, systems and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates orthopedic devices such as alignment guide and cut guides and related components, methods and systems for performing a resection to a bone. The alignment guides disclosed herein can serve as marking tools according to various examples.

Figure 1A:
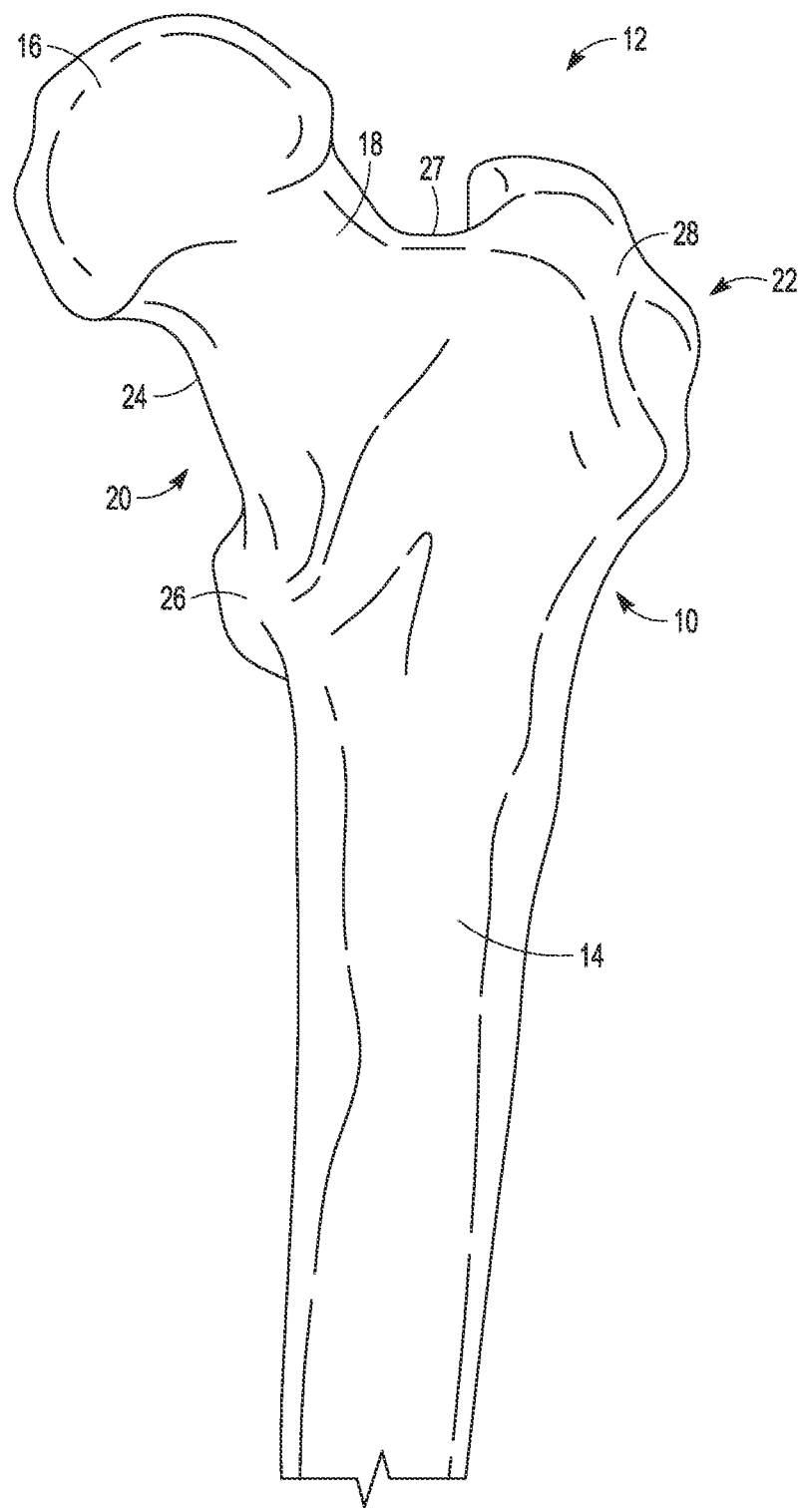
FIG. 1A is a perspective view of a proximal portion of an unresected femur having a femoral head, in accordance with an example of the present disclosure.

FIG. 1A shows a bone 10 comprising a proximal end portion 12 of a femur 14. The femur 14 can have a head 16, a neck 18, a medial portion 20 and a lateral portion 22. The medial portion 20 includes a first saddle 24 and a lesser trochanter 26. The lateral portion 22 includes a second saddle 27 and a greater trochanter 28.

The head 16 can be the proximal most part of the femur 14 and can be attached to the remainder of the femur 14 by the neck 18. The medial portion 20 can include the lesser trochanter of the femur 14 and surface portions surrounding the lesser trochanter 26 such as the first saddle 24 of the neck 18.

Figure 1B:
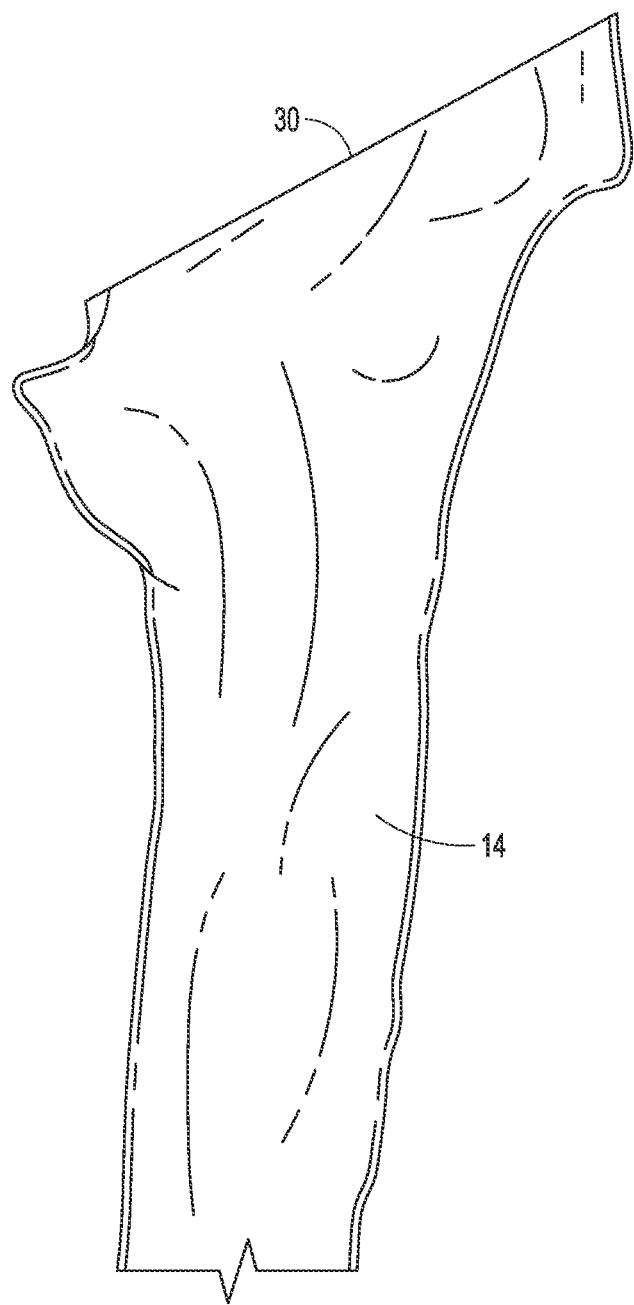
FIG. 1B is a perspective view of the proximal portion of the femur having undergone a neck resection using the devices and techniques disclosed herein to remove part of the greater trochanter, a femoral neck and femoral head, in accordance with an example of the present disclosure.

FIG. 1B shows a planar resection 30 that has been performed on the femur 14. This resection 30 can be facilitated by one or more of the orthopedic assemblies disclosed herein. For example, the resection 30 can be guided by the orthopedic assembly as will be described and illustrated subsequently in reference to FIGS. 3-7D. However, other orthopedic tools disclosed herein can provide an alignment guide that facilitates marking the femur 14 to make the resection 30.

In the case of the example of FIGS. 3-7D, the surgeon can optionally make by hand (unguided) resection(s), as desired, such as the resection 30. These resections can be directed or otherwise indicated with markings.

Following resection, a broach can be inserted through the neck resection 30 to prepare an intramedullary canal of the femur 14 for receiving a femoral stem of a femoral implant.

Figure 2:
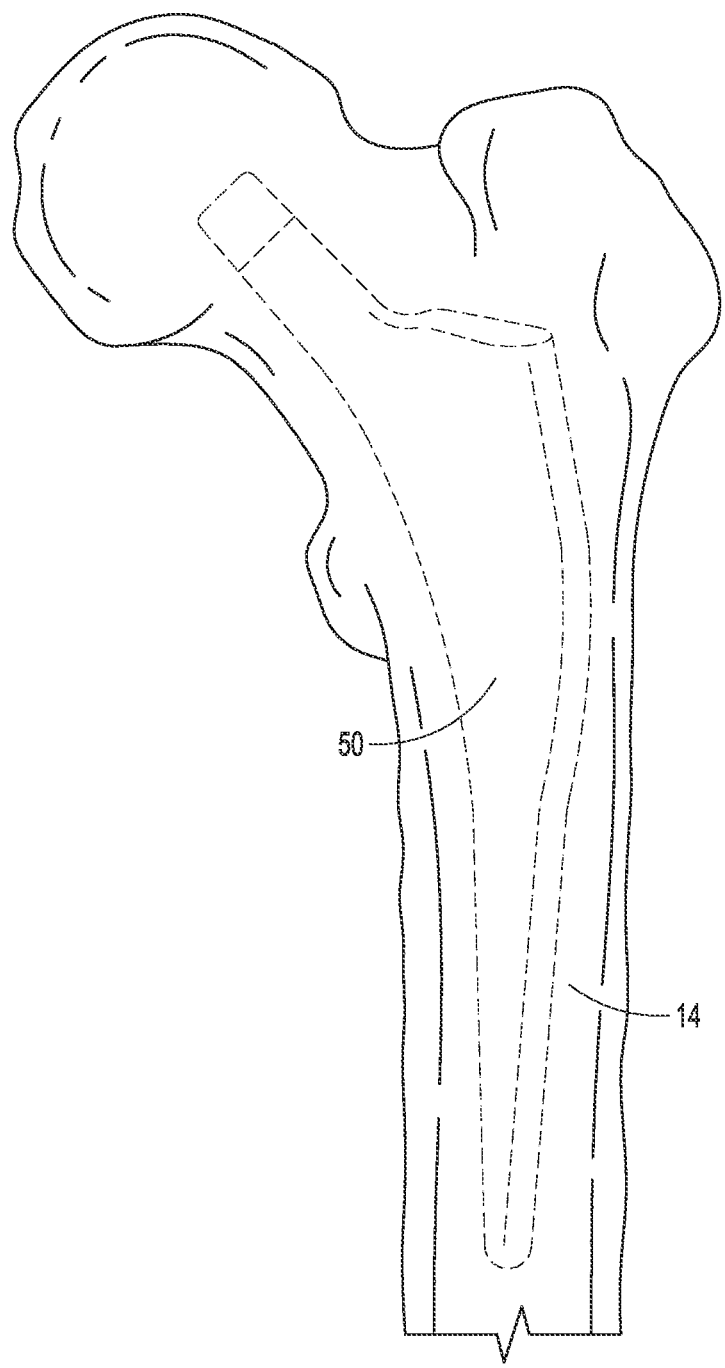
FIG. 2 is the femur of FIG. 1A or 1B or a virtual representation of a femur further illustrating a virtual representation of a broach inserted therein, in accordance with an example of the present disclosure.

Virtual surgical planning tools such as those discussed herein can be utilized to virtually represent this broach and the desired position for this broach as shown in various of the FIGURES such as FIG. 2, for example. Various other instruments not specifically shown can be utilized to properly size, select and couple the femoral implant to the femur 14 including femoral stem broaches, broach insertion tools, trunnions, trial femoral heads, etc., which are commercially available from Zimmer Biomet, Warsaw, Ind.

FIG. 2 shows a virtual representation of a broach 50 positioned within the femur 14. The positioning of the broach 50 can be patient-specific according to some examples to achieve a desired position. The positioning of the broach 50 can be aided by the use of computer-assisted image methods based on two-dimensional or three-dimensional images of the patient's bones and/or adjacent anatomy generated by magnetic resonance imaging ("MRI"), computer tomography ("CT"), ultrasound, X-ray, or other medical imaging techniques. Various computer aided drafting ("CAD") programs and/or other software can be utilized for the image reconstruction of the anatomy (in three-dimensions or two-dimensions) from the medical scans of the patient, such as, for example, commercially available software. The broach 50 can be rendered and positioned in this manner as shown in FIG. 2.

Various pre-operative planning procedures and related patient-specific instruments are disclosed in commonly assigned and pending or now issued U.S. patent application Ser. No. 11/756,057, filed May 31, 2007; U.S. patent application Ser. No. 11/971,390, filed on Jan. 9, 2008; U.S. patent application Ser. No. 12/025,414, filed on Feb. 4, 2008; U.S. patent application Ser. No. 12/039,849 filed on Feb. 29, 2008; U.S. patent application Ser. No. 12/103,824, filed Apr. 16, 2008; U.S. patent application Ser. No. 12/371,096, filed Feb. 13, 2009; U.S. patent application Ser. No. 12/483,807, filed Jun. 12, 2009; U.S. patent application Ser. No. 12/872,663, filed Aug. 31, 2010; U.S. patent application Ser. No. 12/973,214, filed Dec. 20, 2010; and U.S. patent application Ser. No. 12/978,069, filed Dec. 23, 2010. The disclosures of the above applications are incorporated herein by reference.

Figure 3:
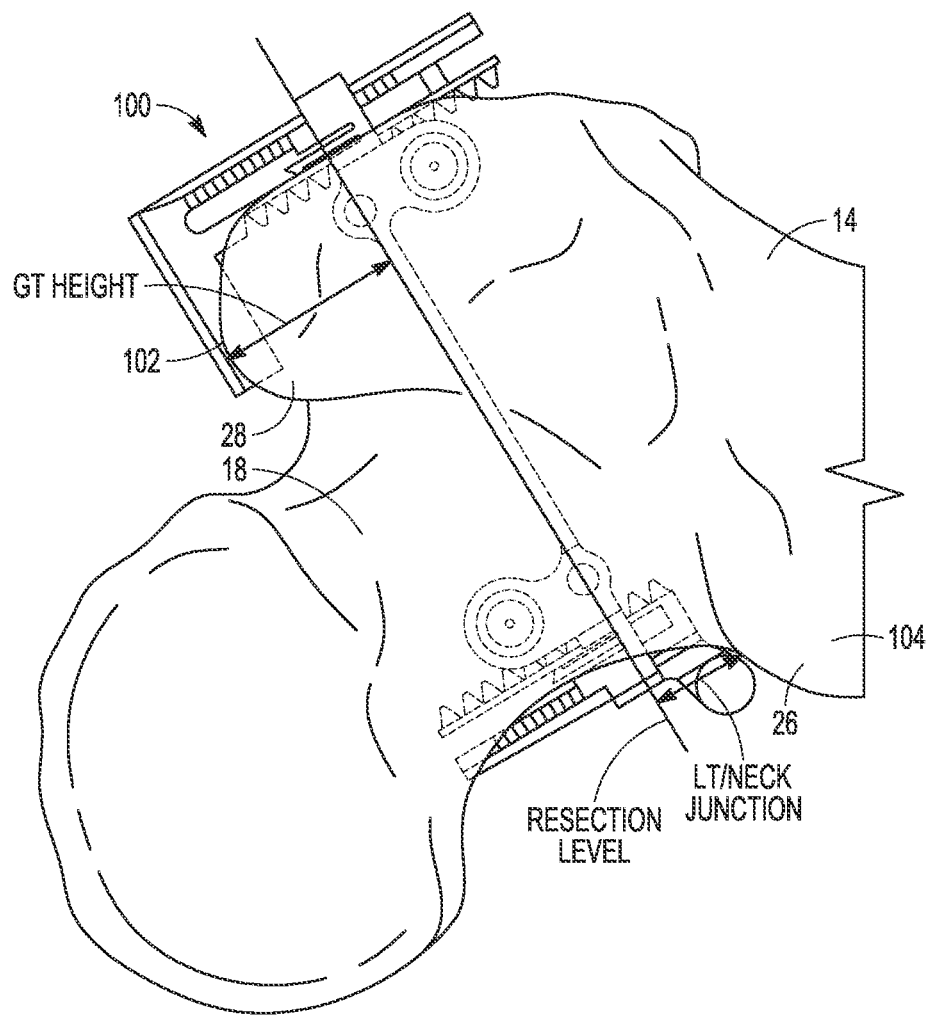
FIG. 3 illustrates a methodology with an orthopedic assembly shown in phantom whereby positioning devices of the orthopedic assembly are seated on the proximal femur to identify a resection line, in accordance with an example of the present disclosure.
Figure 4:
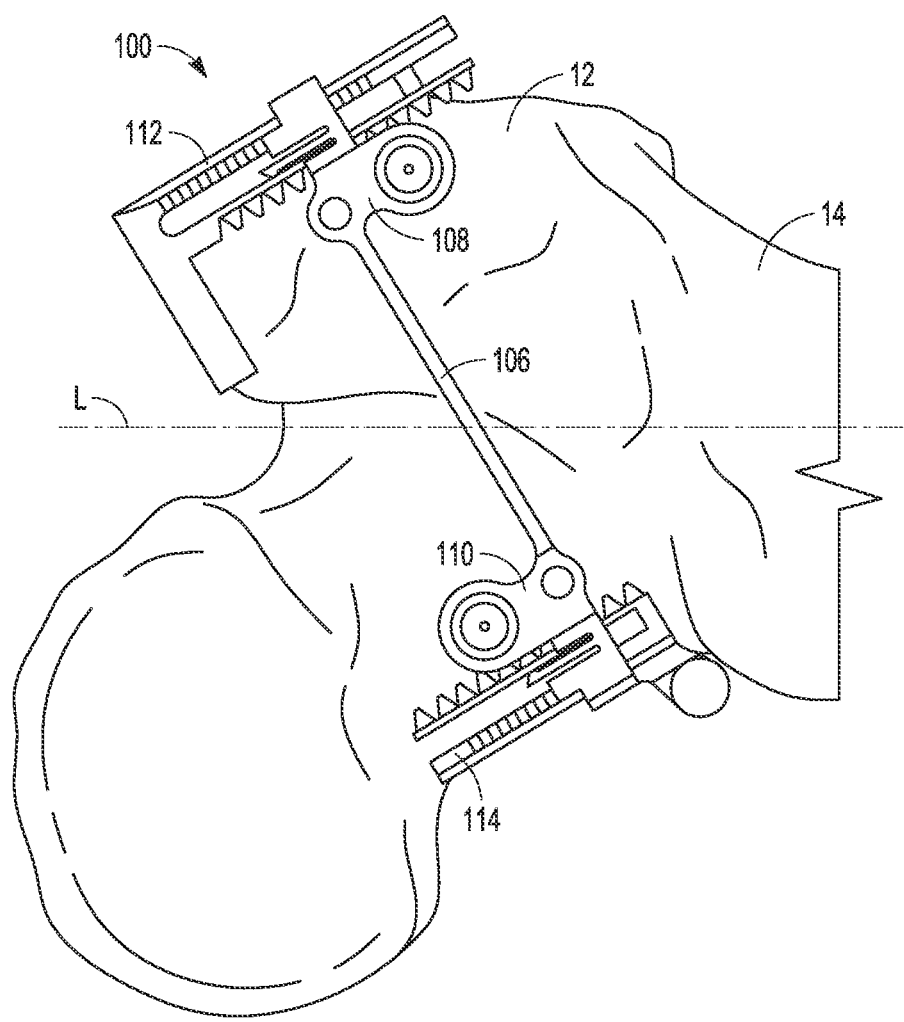
FIG. 4 is a perspective view of the orthopedic assembly secured to the unresected femur of FIG. 1A, the orthopedic assembly including two positioning devices and a cut guide, in accordance with an example of the present disclosure.

FIGS. 3 and 4 show an orthopedic system 100 coupled to the femur 14 in a desired position prior to making the neck resection 30 of FIG. 1B. FIG. 3 shows the orthopedic system 100 in phantom to further illustrate a resection level and measured distances achieved by the orthopedic system 100.

FIG. 3 illustrates one methodology that can be implemented by the orthopedic system 100 with reference to the femur 14. This methodology can be implemented electronically using a computer using CAD and other software and with the systems and methods as further described herein including in reference to FIGS. 4-7D.

FIG. 3 shows a first distance labeled as "GT Height". This first distance can be measured from a proximal most surface 102 of the greater trochanter 28 to a resection line (labeled "Resection Level" in FIG. 3). The resection line can correspond to the resection 30 of FIG. 1B. The position of the resection line can additionally be determined by a second distance labeled "LT/Neck Junction". This second distance can be measured from a location 104 that comprises a junction between the neck 18 of the femur 14 and the lesser trochanter 26.

FIG. 4 shows the orthopedic system 100 that can achieve the methodology of FIG. 3. The orthopedic system 100 can include a body 106 having a longitudinal extent with a first end 108 opposing a second end 110. The body 106 can be configured to extend across the proximal end portion 12 of the femur 14. The body 106 can be configured as a cut guide as further discussed herein. The orthopedic system 100 can include a first portion 112 configured to moveably couple to the first end 108 of the body 106. The first portion 112 can be configured to reference the proximal most surface 102 of the 14. As shown in FIG. 4, the first portion 112 can be positioned to a first side of a longitudinal axis L of the femur 14.

The orthopedic system 100 can include a second portion 114 configured to moveably couple to the second end 110 of the body 106. The second portion 114 can be configured to reference a second surface (i.e. the location 104) of the of the femur 14. The second portion 114 can be positioned to a second side of the longitudinal axis L of the femur F.

As further illustrated in FIGS. 7A-7D, the first distance of FIG. 3 as measured by the first portion 112 can be indicated by first indicia of the orthopedic system 100. Similarly, the second distance of FIG. 3 as measured by the second portion 114 can be indicated by second indicia of the orthopedic system 100. The first and/or second distances can be determined pre-operatively, for example.

Thus, in some examples, the orthopedic system such as the one previously described in FIGS. 3 and 4 can be used as part of systems and methods of generating and outputting data comprising position settings for purposes of tailoring the orthopedic system 100 such that the body 106 can be used to create a patient appropriate resection having a desired location, length, and/or orientation. It should be noted, however, that the virtual surgery planning systems and methods discussed herein are optional and the orthopedic system 100 can be used without them.

As discussed previously, the embodiments discussed herein including the orthopedic system 100 can be aided by the use of two-dimensional images such as X-rays or computer-assisted image methods based on two-dimensional or three-dimensional images of the patient's bones and/or adjacent anatomy generated by medical imaging techniques. CAD or other software programs can be utilized for the image reconstruction of the anatomy (in three-dimensions or two-dimensions) from the medical scans of the patient as desired.

The systems and methods disclosed herein can draw upon preoperative surgical plans. These plans can be formulated for a specific patient. A preoperative surgical plan can encompass virtual surgery planning with the aid of a computer, as will be discussed subsequently. The systems and method can allow for interactive input from the patient's physician or other medical professional according to some examples. Imaging data from medical scans of the relevant anatomy of the patient can be obtained at a medical facility or doctor's office, using any of the medical imaging techniques discussed previously. The imaging data can include, for example, various medical scans of a relevant bone (here the femur 14), bones or other relevant portion of the patient's anatomy, as needed for virtual anatomy modeling and, optionally, for virtual determination of resection size, shape (e.g. angle) and relative orientation. The imaging data, thus obtained, and other associated information can be used to construct a computer (digital) image of the anatomy of the patient. The preoperative surgical plan can further include the identification and selection of particular bone portions that need to be removed or retained, virtual orientation of the orthopedic device as disclosed herein on the femur, virtual implantation of an orthopedic system, etc. Such selections such as the length, and/or the orientation of the resection can be made to best match the patient's anatomical need. For example, the disclosed orthopedic system including the body can be configured as a cut guide and can have the first portion and the second portion with settings to adjust the position of the body. Such settings can be standard settings that are not necessarily patient-specific but can be adjusted based on data output to the physician comprising various size settings that most closely match the needs of the patient based upon the patient's anatomy. These size settings can be visually displayed to the physician as part of the surgical plan. Thus, referring back to the example of FIGS. 1B-4, the resection 30 (FIG. 1B) position, orientation, etc. can be virtually determined and the first distance (the GT Height) can be virtually determined and displayed. If the first distance is determined to be 10 mm, the virtual surgery planning aid would display a setting of 10 mm indicating the body 106 and the first portion 112 should be set to the setting of 10 mm. A similar technique can be followed with regard to the second distance comprising the LT/Neck Junction. This second distance can be virtually determined and displayed. If the second distance is determined to be 5 mm, the virtual surgery planning aid would display a setting of 5 mm indicating the body 106 and the second portion 114 should be set to the setting of 5 mm. In this manner the resection line ("Resection Level" of FIG. 3) can be achieved.

The virtual model of the patient's anatomy can be viewed on a computer display or other electronic screen and can also be reproduced as a hard copy on disk or other medium and viewed by direct or indirect or backlight illumination. The model can be sized for viewing on any appropriate screen size and may be cropped, rotated, etc., as selected by the individual (e.g., the physician) viewing the screen. The three-dimensional model can illustrate diseased bone that should be removed and can identify the shape and orientation of the resection(s) to be used in removal of the diseased bone, etc. The three-dimensional model can further illustrate the orthopedic assembly overlaid on the bone such as in FIGS. 3-6 and can show the relevant cuts according to one example.

According to one example, the orthopedic system 100 can be fabricated with various standard markings or indicia indicative of various lengths, such as A, B, C, D for indicia 118C. A marking "A" of the orthopedic system 100 can correspond to a virtual output "A" displayed to the user. Put another way, the orthopedic system 100 can be set to a most appropriate length (such as "A") as indicated or suggested by the system output.

Figure 5:
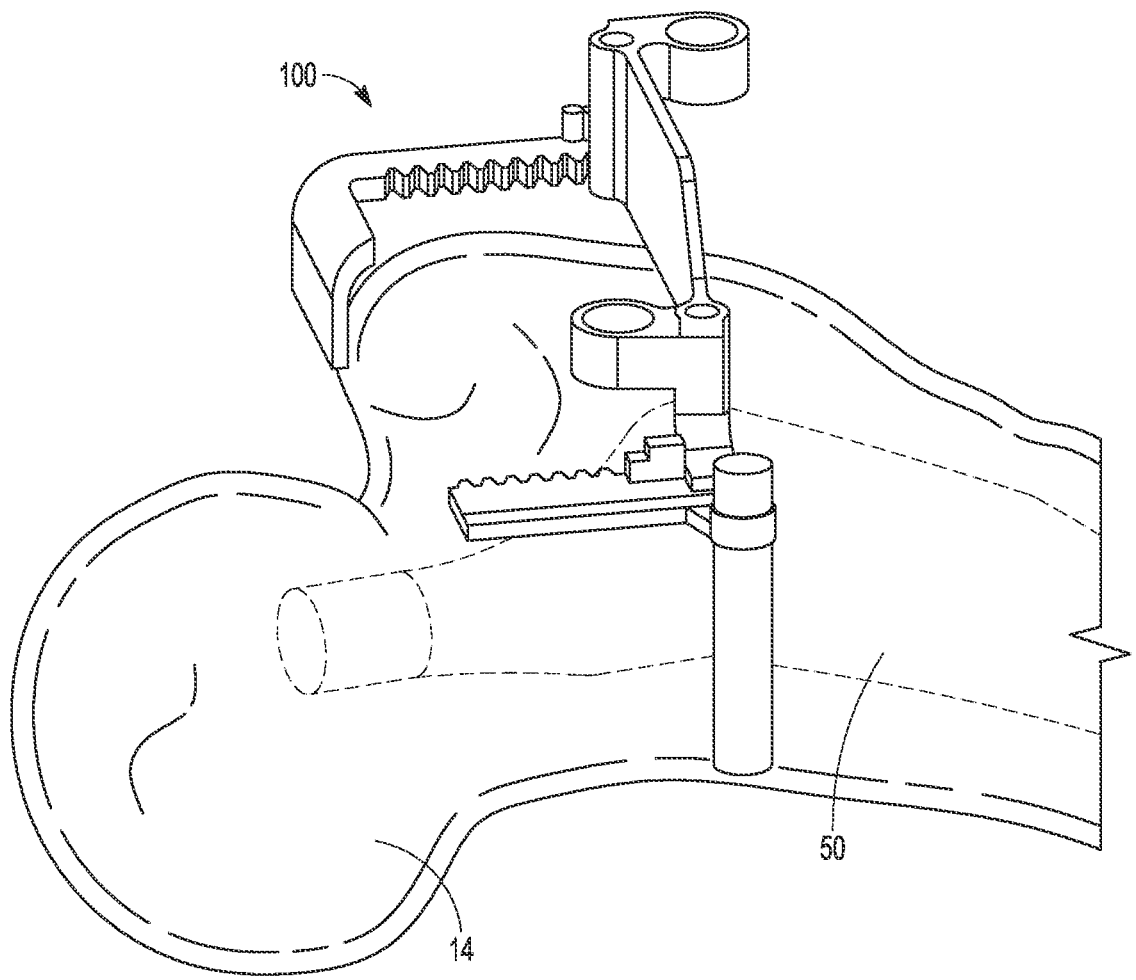
FIG. 5 is a perspective view of the orthopedic assembly of FIG. 3 mounted to the proximal femur, in accordance with an example of the present disclosure.
Figure 6:
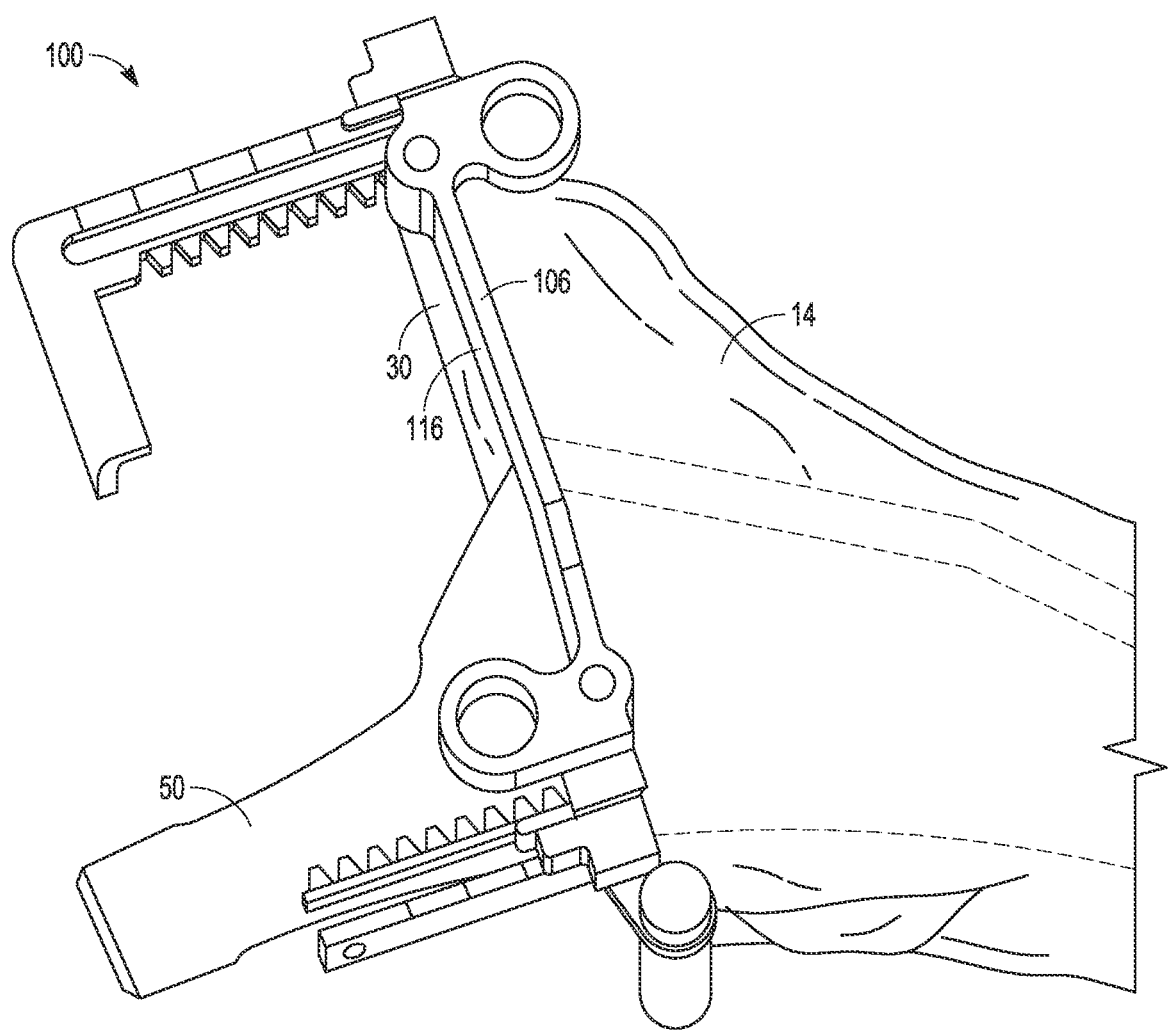
FIG. 6 is a perspective view showing the orthopedic assembly acting as a guide to make a resection to the proximal femur, in accordance with an example of the present disclosure.

FIGS. 5 and 6 show further views of the orthopedic system 100 as rendered virtually via software. The orthopedic system 100 is illustrated mounted to a virtual rendering of the femur 14 with the broach 50. FIG. 6 shows a virtual representation of the resection 30 performed on the femur 14. The resection 30 can align with and be implemented with aid of a surface 116 of the body 106 as shown in FIG. 6 and further described subsequently.

Figure 7A:
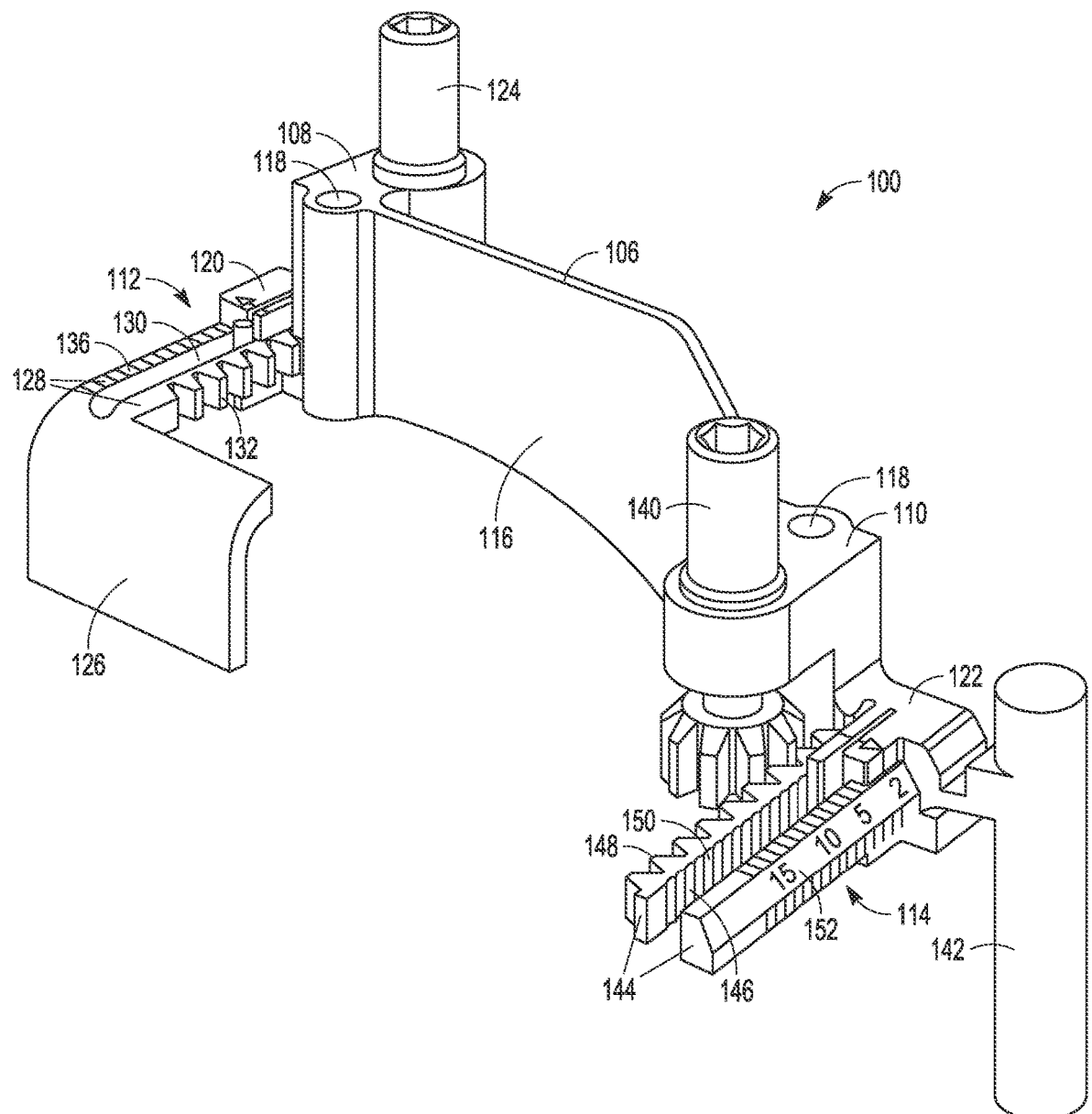
FIGS. 7A-7C are views from various perspectives of the orthopedic assembly of FIG. 3 shown in isolation.
Figure 7B:
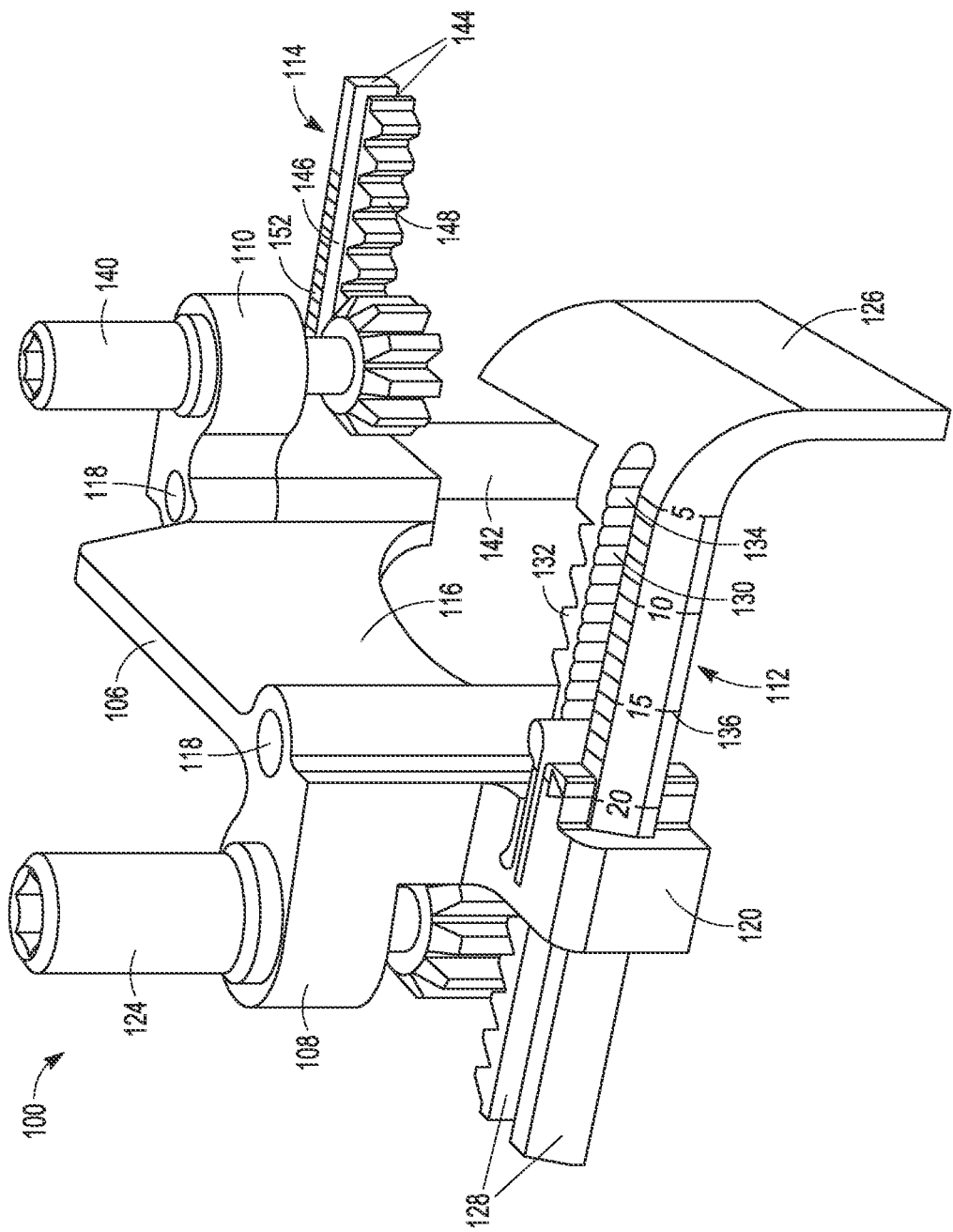
Figure 7C:
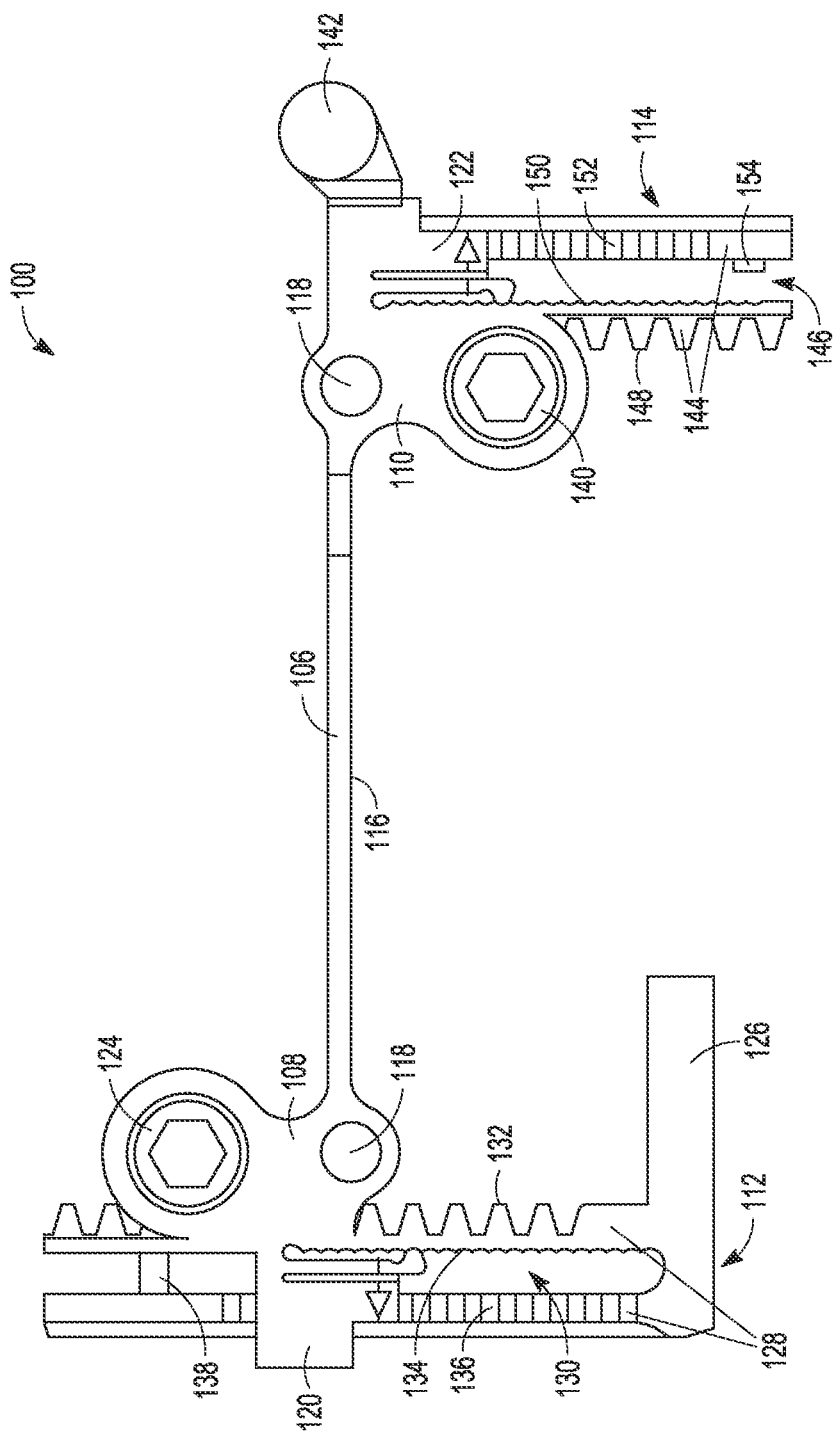

FIGS. 7A-7C show the orthopedic system 100 from various perspectives including a plan view in FIG. 7C. The orthopedic system 100 can include the body 106, the first portion 112 and the second portion 114. The body 106 can include the first end 108, the second end 110, the surface 116, one or more apertures 118, a first connection feature 120 and a second connection feature 122. The first portion 112 can include a first actuator 124, a paddle 126, arms 128, a track 130, teeth 132, detents 134 (FIGS. 7B and 7C), first indicia 136 and a stop 138 (FIG. 7C). The second portion 114 can include a second actuator 140, a projection 142, arms 144, a track 146, teeth 148, detents 150, second indicia 152 and a stop 154 (FIG. 7C).

The body 106 can have a longitudinal length from the first end 108 to the second end 110. The surface 116 can extend along the longitudinal length and can be located between the first end 108 and the second end 110. The surface 116 can be a proximal surface when the body 106 is mounted to the femur, for example. The surface 116 can be substantially flat to act as a guide in performing resection.

The one or more apertures 118 can pass through the body 106 and can be configured to receive a pin, bone screw, etc. that can be used to affix the body 106 to the bone. The one or more apertures 118 can comprise two apertures with one of the two apertures located at or adjacent the first end 108 and the second of the two apertures located at or adjacent the second end 110.

The first connection feature 120 can be located at the first end 108. The second connection feature 122 can be located at the second end 110. The first connection feature 120 can include a slot configured to receive part of the first portion 112 and an aperture configured to receive a second part of the first portion 112. The second connection feature 122 can be configured in a similar manner as the first connection feature 120. Thus, the second connection feature 122 can have include a slot configured to receive part of the second portion 114 and an aperture configured to receive a second part of the second portion 114.

In particular, the first connection feature 120 with the slot can be configured to receive the arms 128 of the first portion 112. The aperture of the first connection feature 120 can be configured to receive the first actuator 124. The second connection feature 122 with the slot can be configured to receive the arms 144 of the second portion 114. The aperture of the second connection feature 122 can be configured to receive the second actuator 140.

The first portion 112 can be configured as a rack and pinion with the first actuator 124 configured as the pinion and the arms 128, the track 130 and the teeth 132 configured as the rack to allow the first portion 112 to be movable relative to the body 106. The second portion 114 can be configured in a similar manner with the second actuator 140 as the pinion and the arms 144, the track 146 configured as the rack such that the second portion 114 can be movable relative to the body 106.

The first actuator 124 can extend through the body 106 and can have an engagement feature with teeth configured to engage the teeth 132. The paddle 126 can be located on an end of the first portion 112 and can connect with the arms 128. The arms 128 can extend parallel with one another spaced by the track 130 that comprises a slot. The teeth 132 can be arranged in a linear manner along an inner facing edge of one of the arms 128. The teeth 132 are engageable by mating teeth of the first actuator 124. The first indicia 136 can located along one or more of the arms 128. The detents 134 can be arranged along the track 146. FIG. 7C shows the stop 138 can be located within the track 130.

In operation, the first portion 112 can be moveable relative to the body 106 via the track 130 and the first actuator 124 engaging the teeth 132. The paddle 126 can be configured to engage the proximal surface of the greater trochanter as previously illustrated. The stop 138 can limit extension of the first portion 112 from the body 106 so that the first portion 112 does not decouple from the body 106.

The second actuator 140 can extend through the body 106 and can have an engagement feature with teeth configured to engage the teeth 148. The projection 142 can be located on an end of the second portion 114 and can connect with the arms 144. The arms 144 can extend parallel with one another spaced by a track 146 that comprises a slot. The teeth 148 can be arranged in a linear manner along an inner facing edge of one of the arms 144. The teeth 148 are engageable by mating teeth of the second actuator 140. The first indicia 152 can be located along one or more of the arms 128. The detents 150 can be arranged along the track 146. FIG. 7C shows the stop 154 can be located within the track 146.

In operation, the second portion 114 can be moveable relative to the body 106 via the track 146 and the second actuator 140 engaging the teeth 148. The projection 142 can be configured to engage the proximal surface of the bone at the junction of the lesser trochanter and neck as previously illustrated. The stop 154 can limit extension of the second portion 114 from the body 106 so that the second portion 114 does not decouple from the body 106.

Figure 7D:
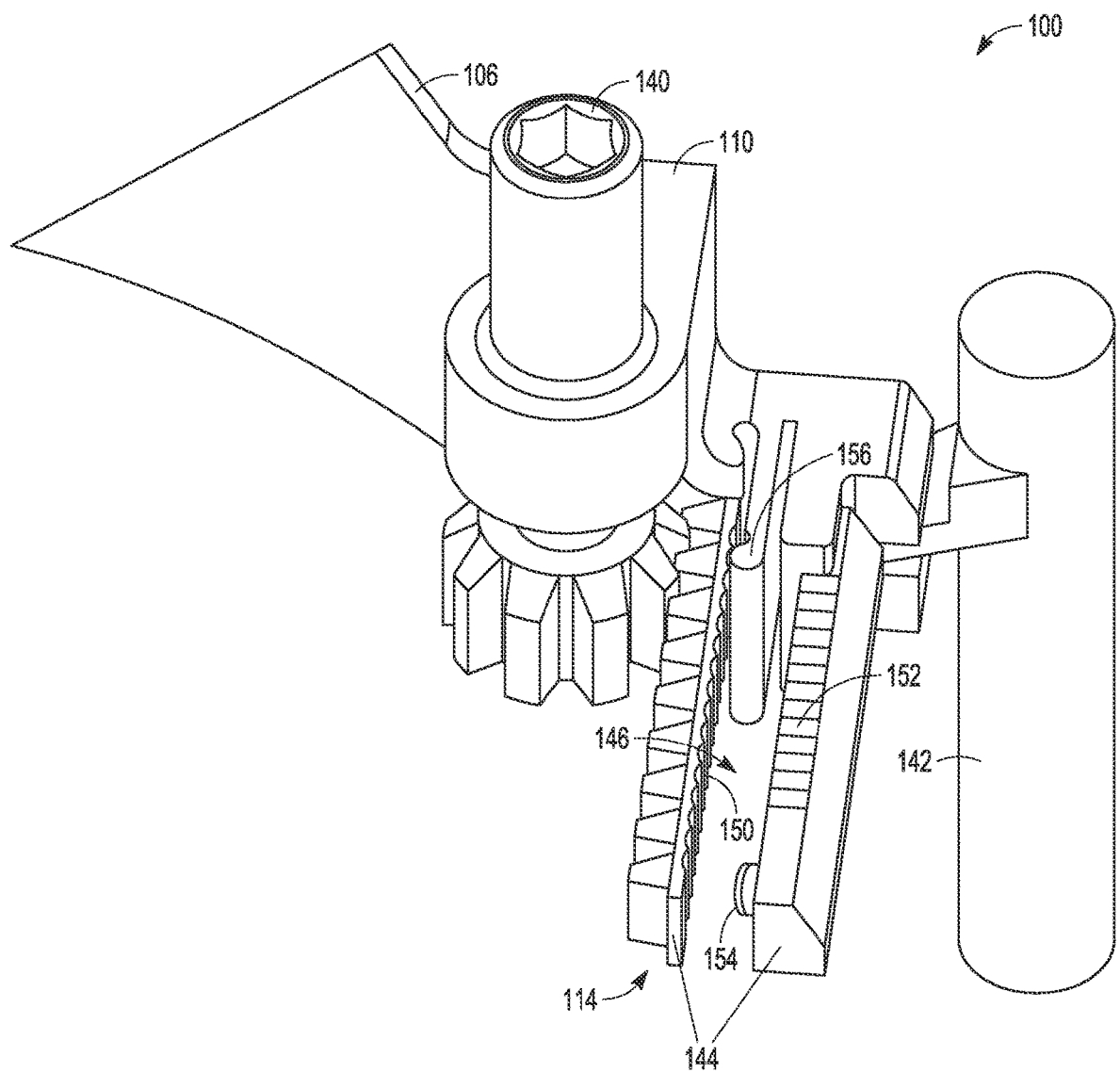
FIG. 7D is an enlarged view of a portion the orthopedic assembly of FIG. 7A.

FIG. 7D shows an enlarged view of the second portion 114 and the second end 110 of the body 106. The second portion 114 can include the second actuator 140, the projection 142, arms 144, the track 146, the teeth 148, the detents 150, the second indicia 152 and the stop 154 as previously discussed.

FIG. 7D shows the detents 150 are engageable by a finger 156 of the body 106. The finger 156 can be spring biased to engage with one or more of the detents 150. This engagement can facilitate locking/holding a position of the second portion 114 relative to the body 106. The detents 134 of the first portion 112 can be engaged by a finger of the first end in a similar manner.

Figure 8:
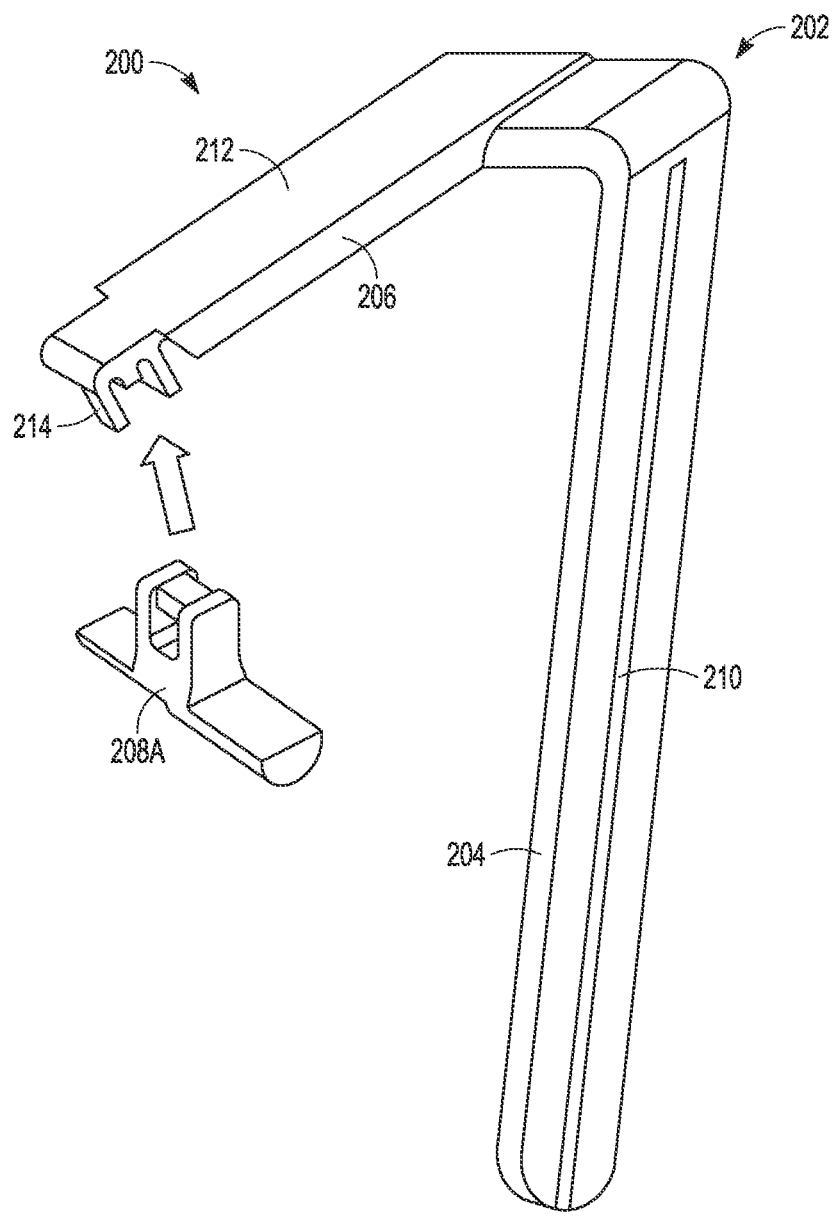
FIG. 8 is a perspective view of a marking tool, in accordance with an example of the present disclosure.
Figure 8A:
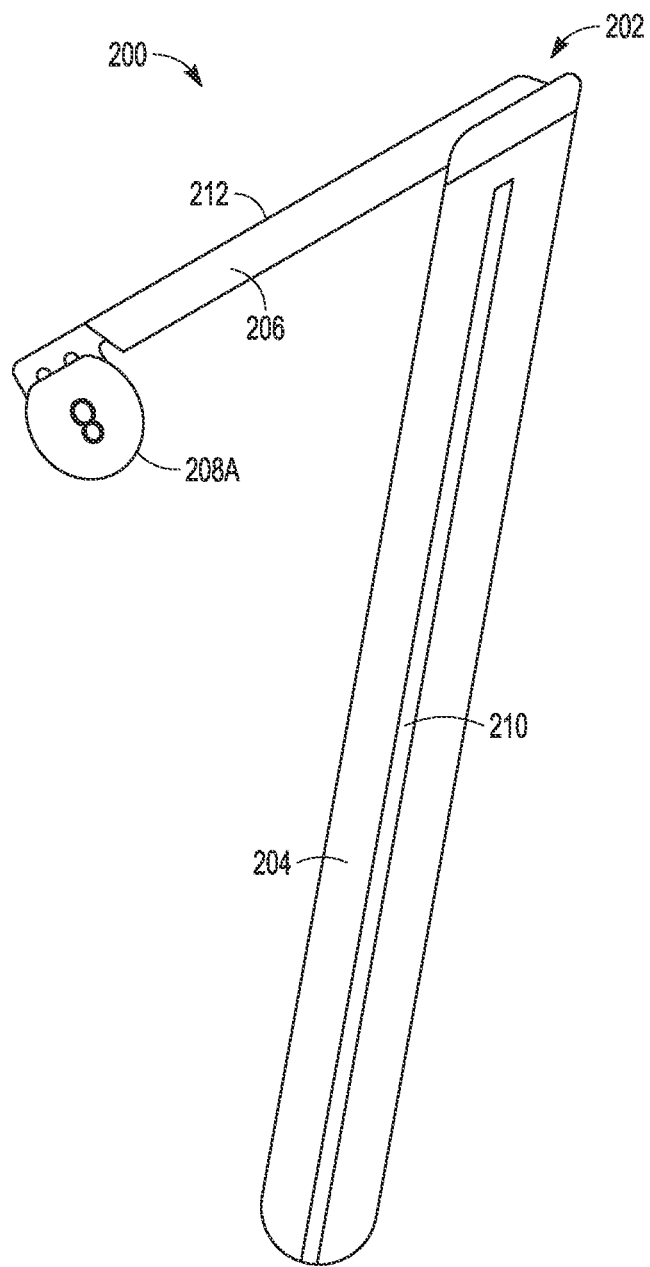
FIG. 8A is an exploded view of the marking tool showing a shim and a main body, in accordance with an example of the present disclosure.
Figure 9A:
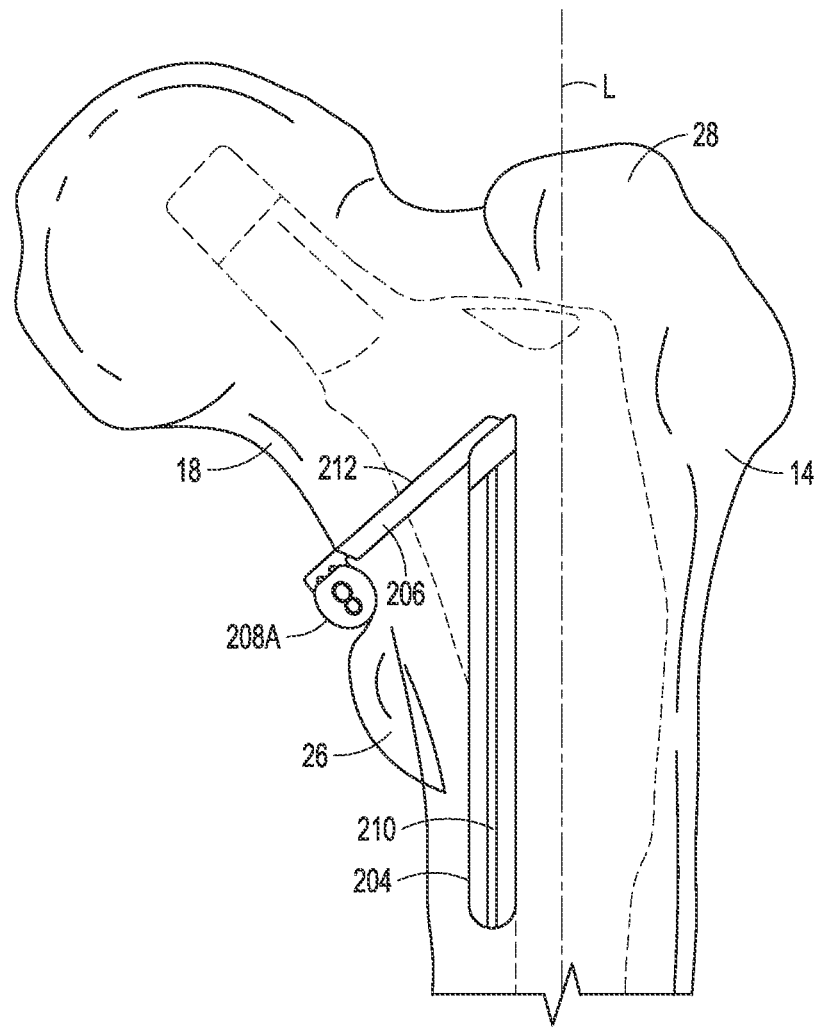
FIGS. 9A and 9B are views from various perspectives of the marking tool of FIG. 8.
Figure 9B:
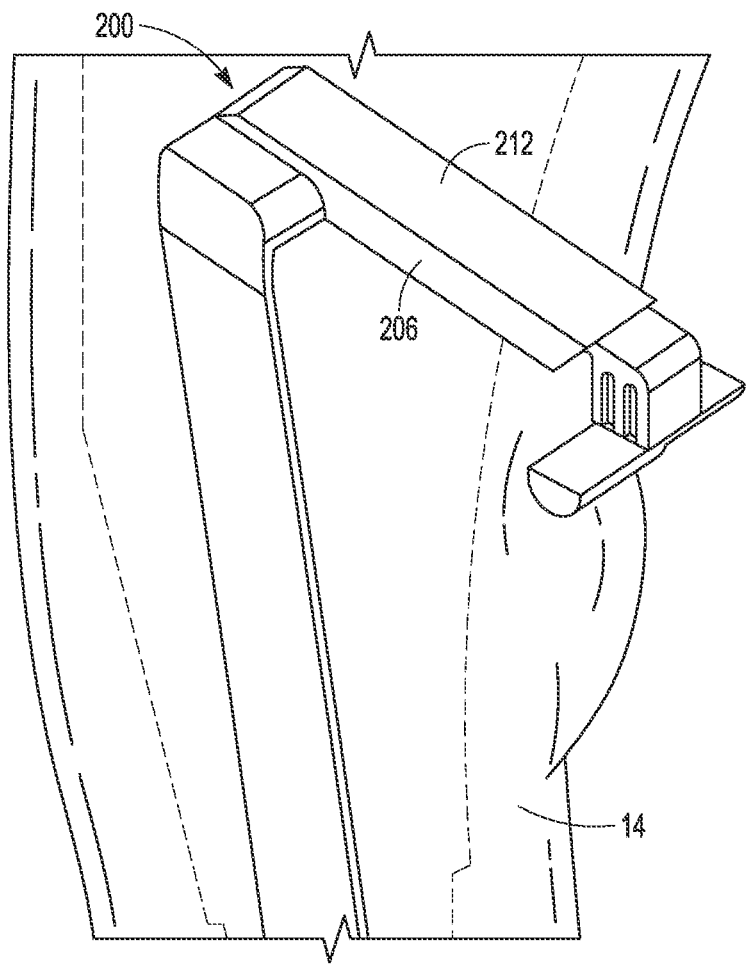

FIGS. 8-9B show an orthopedic system 200 according to another example. This orthopedic system 200, when assembled, can act as a marking tool as further described and illustrated herein. The orthopedic system 200 can include an assembly 202 that has a handle 204 and an arm 206. The system 200 can also include a plurality of shims (only one shim 208A is illustrate in FIGS. 8 and 8A).

The arm 206 can project laterally from the handle 204. The handle 204 can have an elongate shape with the arm 206 positioned at a top thereof. The handle 204 can include indicia 210 such as a line that can be configured to be aligned with the longitudinal axis L of the femur 14 as shown in FIG. 9A. This allows the arm 206 and handle 204 to be oriented with reference to the longitudinal axis L.

The arm 206 can include a proximal surface 212 as shown in FIGS. 8 and 9B that can be configured to guide a marking of the femur 14. In particular, as shown in FIG. 9A, the proximal surface 212 and arm 206 can extend from a first side of the longitudinal axis L of the femur 14 adjacent the junction between the neck 18 of the femur 14 and the lesser trochanter 26 of the femur 14 as shown in FIG. 9A across the femur 14 to a second side of the longitudinal axis L at or adjacent the greater trochanter 28. The proximal surface 212 of the arm 206 can be configured to guide marking of the femur 14 from the first side of the longitudinal axis L adjacent the junction across the femur to the second side of the longitudinal axis L at or adjacent the greater trochanter.

As shown in FIGS. 8 and 8A, the shim 208A can be attachable to and removable from an attachment feature 214 at an end of the arm 206. The shim 208A can be configured to reference the junction between the neck 18 of the femur 14 and the lesser trochanter 26 of the femur 14 as shown in FIG. 9A. The shim 208A can have a known thickness to position the proximal surface 212 a predetermined distance from the junction between the neck 18 of the femur 14 and the lesser trochanter 26 of the femur 14.

Figure 10A:
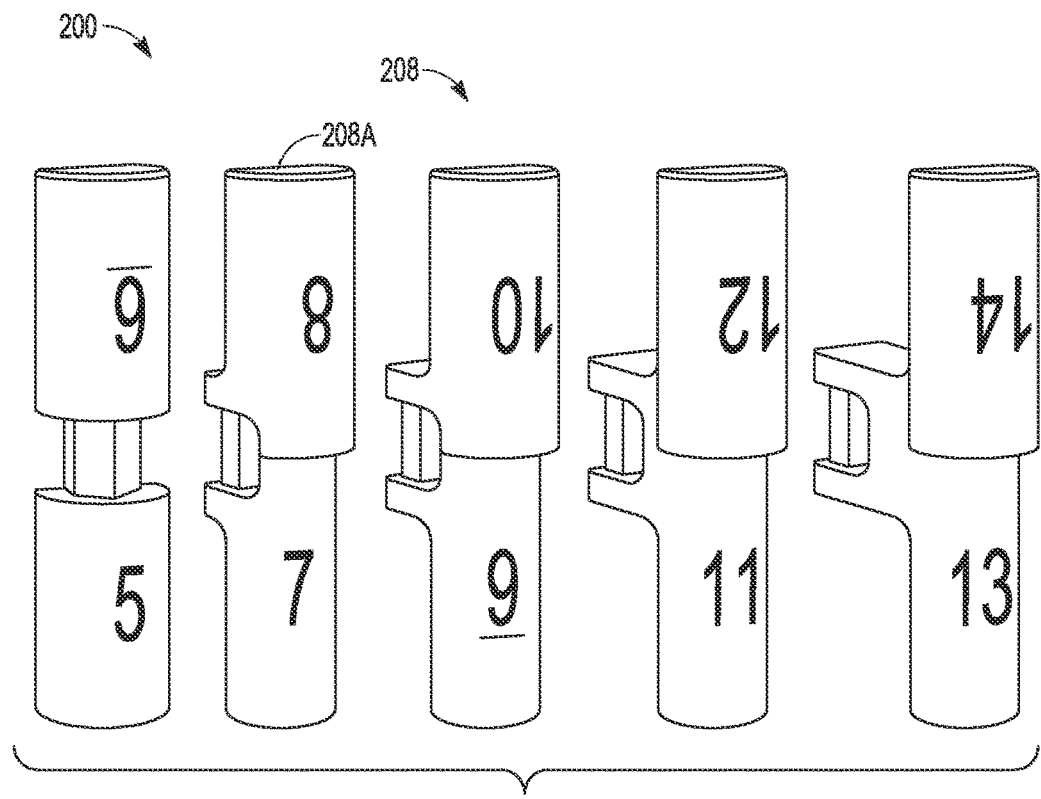
FIGS. 10A and 10B show a system that includes a plurality of the shims, in accordance with an example of the present disclosure.

FIG. 10A shows the orthopedic system 200 can include a plurality of shims 208, including the shim 208A illustrated previously. Each shim of the plurality of shims 208 can be configured to couple with the arm 206 as previously illustrated. The plurality of shims 208 can each of a different thickness (e.g., 5 mm to 14 mm). Each of the plurality of shims 208 can be configured to reference the junction between the neck of the femur and the lesser trochanter of the femur as previously illustrated and described. When one of the plurality of shims 208 is coupled to the arm 206 and positioned to reference the junction, the one of the plurality of shims 208 positions the proximal surface 212 of the arm 206 a predetermined distance from the junction as previously illustrated.

Figure 10B:
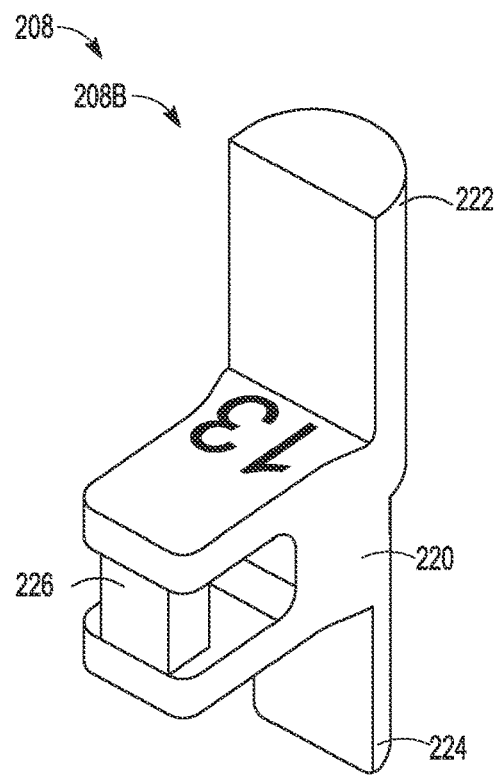

As shown in FIG. 10B, one or more of the plurality of shims 208 (here shim 208B) can have a longitudinal length 220. A first end portion 222 along the longitudinal length 220 can have a first thickness and a second end portion 224 along the longitudinal length 220 opposing the first end portion 222 has a second thickness. The first thickness can differ from the second thickness. With the plurality of shims 208 of FIG. 10A, this different thickness per shim can allow 1 mm increments of thickness to be achieved. For example, the shim 708B can include the first end portion 2222 with a 13 mm thickness (as shown in FIG. 10B), and the second end portion 224 with a 14 mm thickness.

As shown in FIG. 10A, each of shim of the plurality of shims 208 can include one or more connection features 226 for coupling to the arm. The connection feature 226 can allow either the first end portion 222 to be positioned to reference the junction between the neck of the femur and the lesser trochanter of the femur or the second end portion 224 to be positioned to reference the junction between the neck of the femur and the lesser trochanter of the femur.

Figure 11:
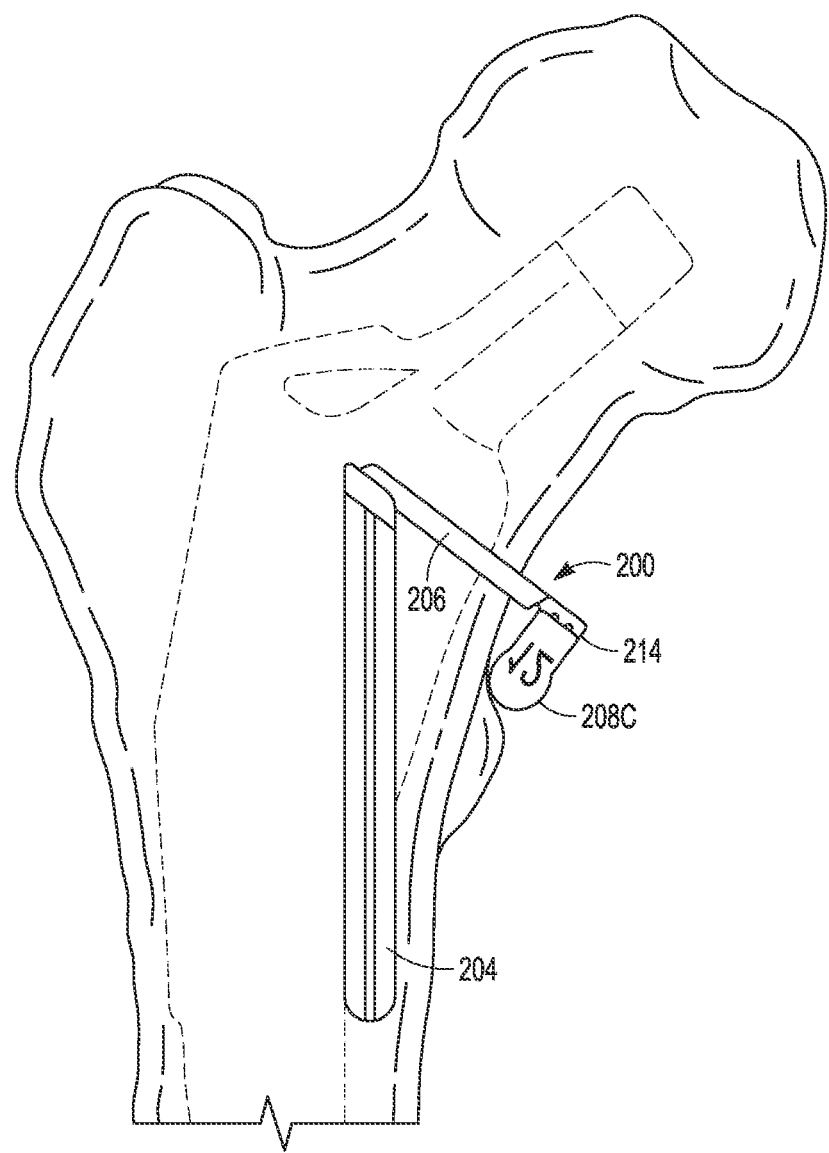
FIG. 11 shows one of the shims from the system of FIGS. 10A and 10B substituted for the shims of FIGS. 9A and 9B, in accordance with an example of the present disclosure.

FIG. 11 shows a shim 208C connected by the connection feature 214 to position the shim 208C with a 12 mm thickness at the junction between the neck of the femur and the lesser trochanter of the femur. It is understood, that if desired, the second shim 208C could be reversed to provide an 11 mm thickness at the junction, for example. It should be understood that the handle 204 and the arm 206 can be configured to be reversible similar to the shims 208 so as to be usable on either a left or right femur. Similarly, the markings such as on the handle 204 can be on the front and back allowing the markings to be used on the left or right femur. Furthermore, it is contemplated that the orthopedic system 200 can draw upon a preoperative surgical plan according to some examples. Such plan can be formulated for a specific patient. However, it is also contemplated that the orthopedic system 200 may not be used with a preoperative surgical plan according to some examples.

Imaging data, as previously discussed can be collected, and can be used to construct a computer (digital) image of the anatomy of the patient as well as the orthopedic system 200. The preoperative surgical plan can include the identification and selection of particular bone portions that need to be removed or retained, virtual orientation of the orthopedic system 200 as disclosed herein on the femur, etc. Selections such as the length, and/or the orientation of the resection can be made to best match the patient's anatomical need. For example, for the disclosed orthopedic system 200 the surgical plan can provide a recommendation of the shim size to select to provide for a desired marking of the femur to achieve to achieve the recommended resection. The shim size selected may not necessarily patient-specific but can be adjusted based on data output to the physician comprising various size settings that most closely match the needs of the patient based upon the patient's anatomy. These size of the shim can be visually displayed to the physician as part of the surgical plan.

Figure 12A:
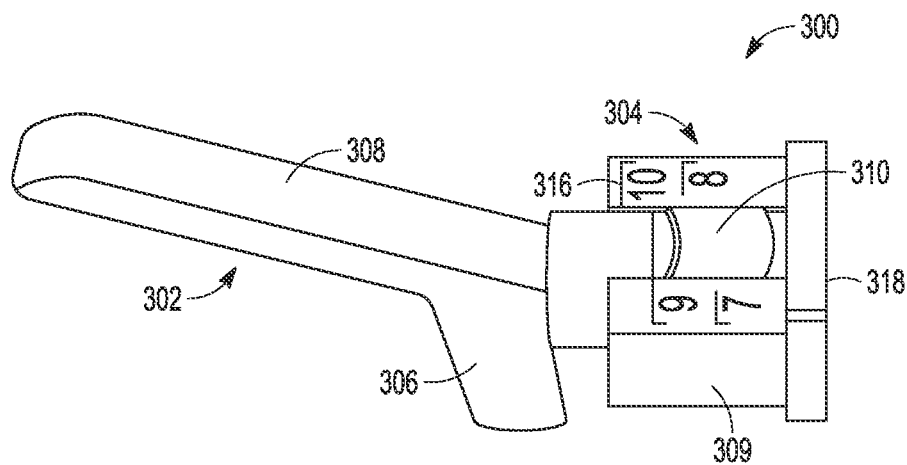
FIGS. 12A and 12B show a second marking tool configured to indicate a depth of the broach, in accordance with an example of the present disclosure.
Figure 12B:
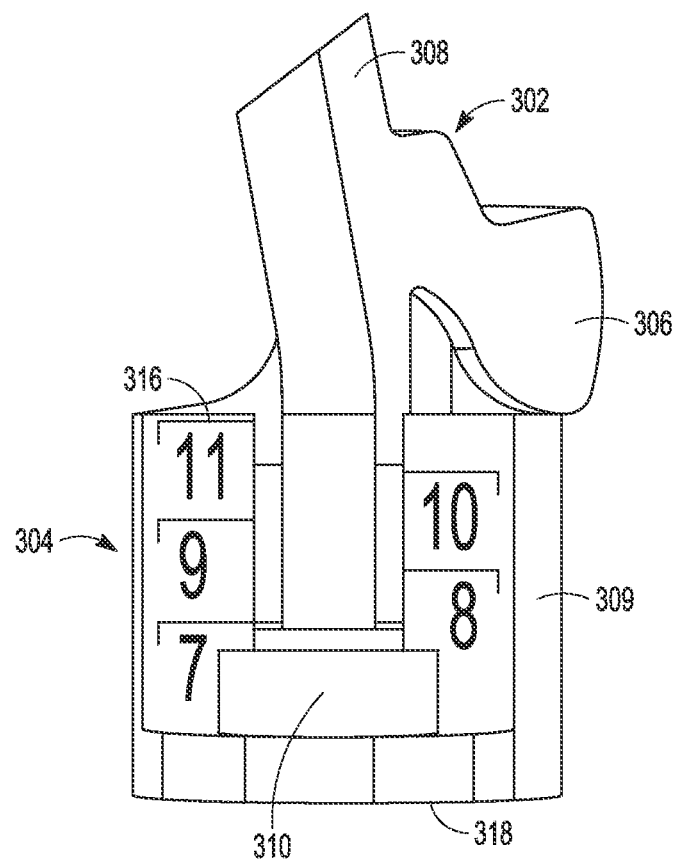
Figure 13:
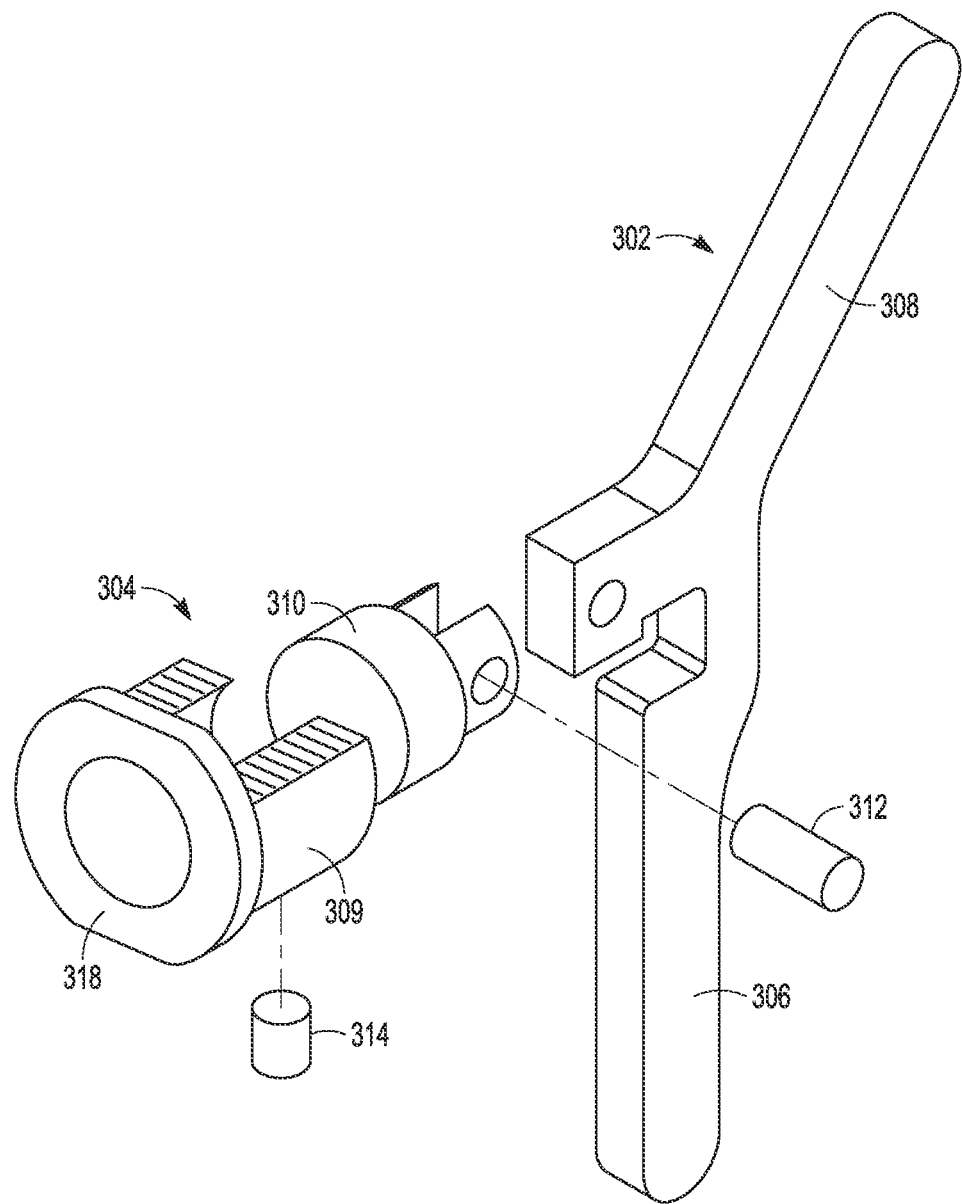
FIG. 13 is an exploded view of the second marking tool of FIGS. 12A and 12, in accordance with an example of the present disclosure.

FIGS. 12A-13 illustrate another example of an orthopedic system 300. The orthopedic system 300 can include an assembly 302 and a body 304. The assembly 302 can include a first arm 306 and a second arm 308. The body 304 can include a moveable portion 309 and a stationary portion 310.

The assembly 302 can be coupled to the body 304 with a pin 312 as shown in FIG. 13. More particularly, the assembly 302 can be coupled to the stationary portion 310 via the pin 312. The stationary portion 310 can comprise a stationary bolt that resides within the moveable portion 309, for example.

The first arm 306 can be coupled to the second arm 308. The first arm 306 can extend away from the second arm 308. The first arm 306 can be configured to rest against a saddle of the neck of the femur as further illustrated herein. The second arm 308 can be configured to be grasped by a surgeon and can be configured to be aligned with the longitudinal axis L of the femur with the first arm 306 placed on the saddle as further illustrated herein.

The moveable portion 309 can be configured to retract and extend along a linear path relative to the stationary portion 310 of the body 304 and the assembly 302. The path of the movement of the moveable portion 309 can be defined by the stationary portion 310. As shown in FIG. 13, the moveable portion 309 can be coupled to the stationary portion 310 via a pin 314. This pin 314 can be received in a slot of the moveable portion 309 allowing the moveable portion 309 to be moveable relative to the stationary portion 310.

As shown in FIGS. 12A and 12B, the body 304 (including one or both of the moveable portion 309 and the stationary portion 310) can include a plurality of indicia 316 configured to indicate a distance between the first arm 306 and a distal end 318 of the body 304 on the moveable portion 309. The distal end 318 can be flared or otherwise shaped to form one or more surfaces configured to engage with a surface of the femur as further illustrated in FIGS. 14A-14C. The distal end 318 can be flat at a distal most surface so as to configured to guide marking or resection of the surface of the femur, for example.

Figure 14A:
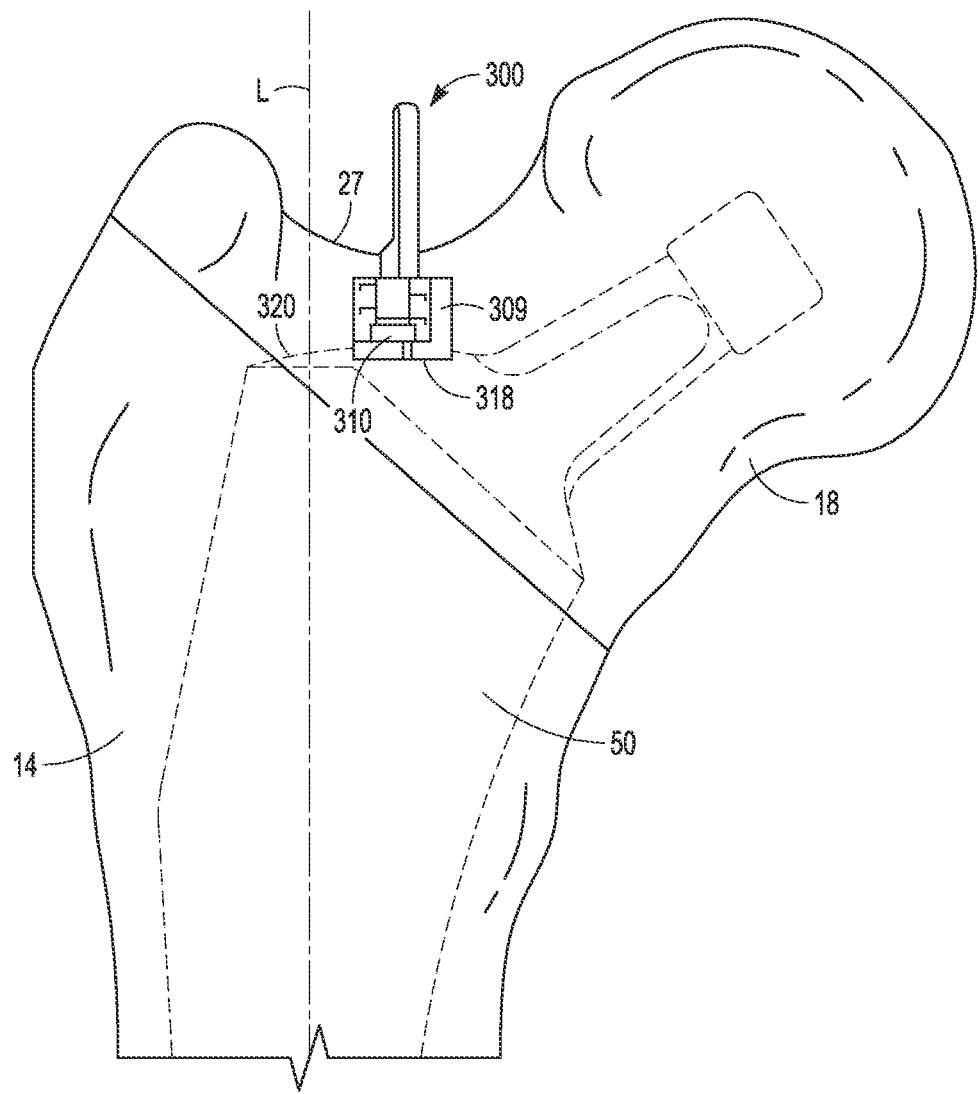
FIGS. 14A-14C show the second marking tool being placed against the bone and being adjusted to indicate a level where a surface of the broach would be located, in accordance with an example of the present disclosure.
Figure 14B:
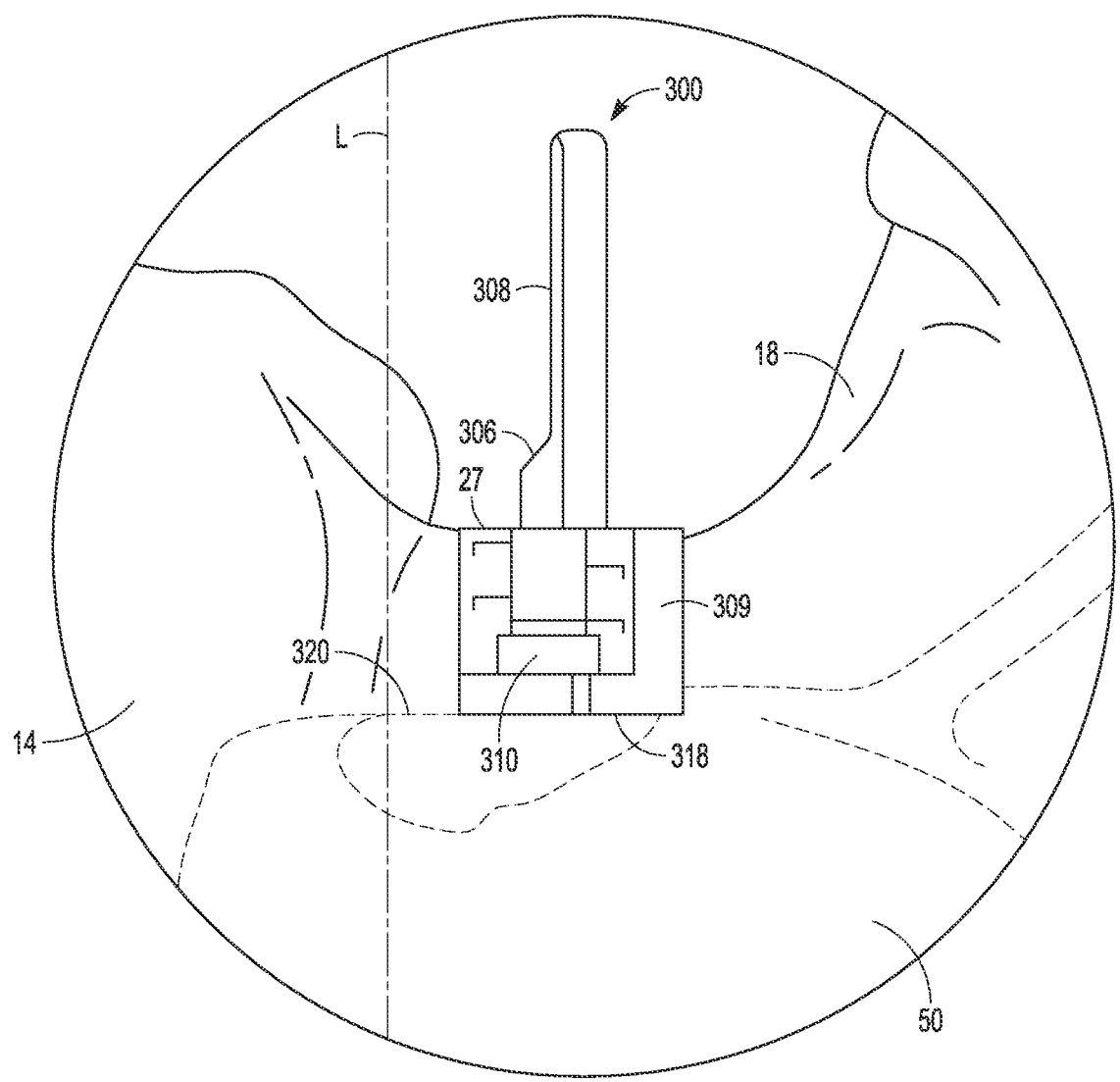
Figure 14C:
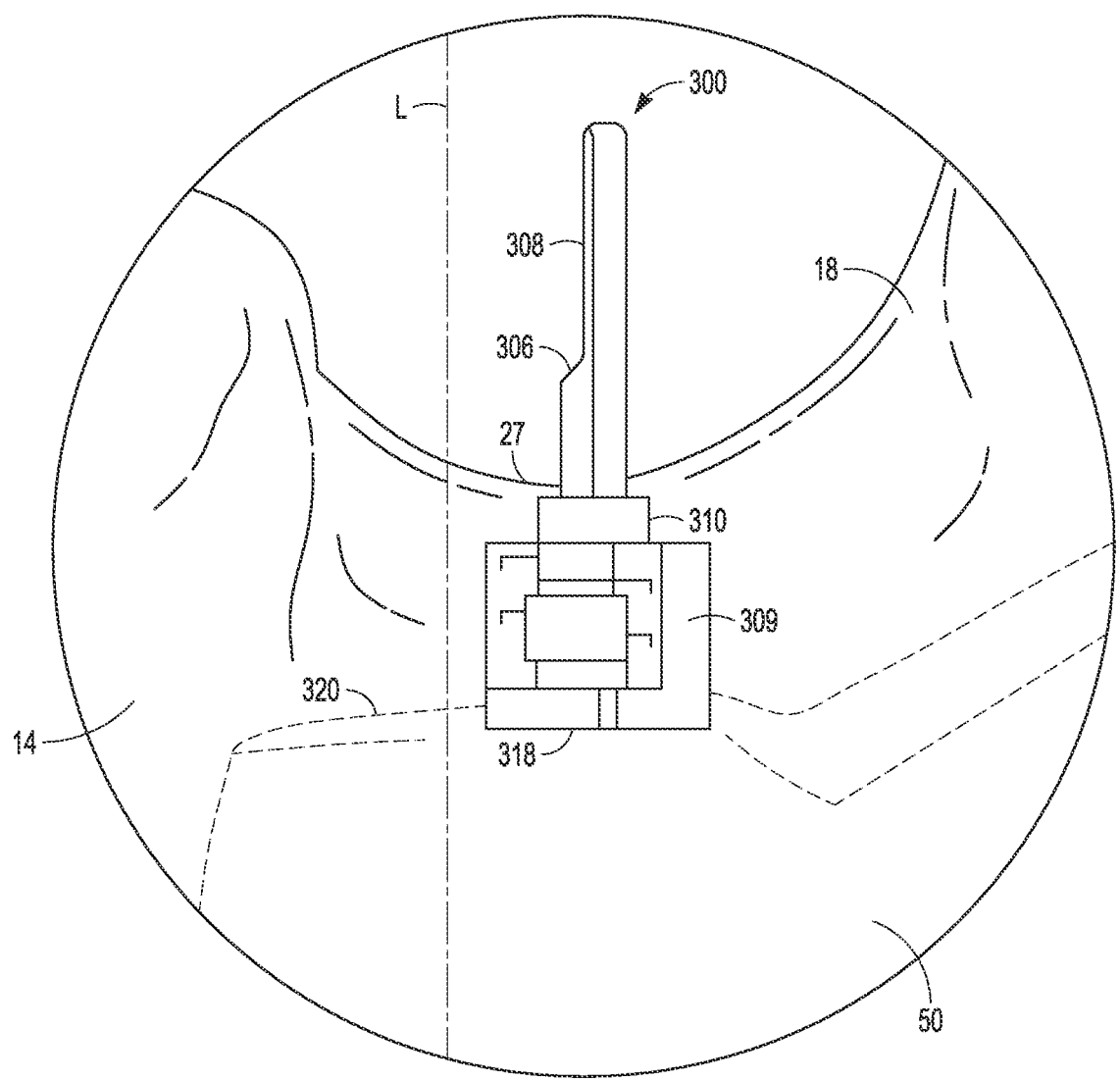

FIG. 14B shows the orthopedic system 300 with the moveable portion 309 in a retracted position relative to the stationary portion 310, the second saddle 27 of the neck 18 of the femur 14, etc. FIGS. 14A and 14C show the moveable portion 309 extended (i.e. moved) to a second position relative to the stationary portion 310, the second saddle 27 of the neck 18 of the femur 14. In the second position, the distal most surface of the distal end 318 can approximate a proximal surface 320 of the broach 50.

FIGS. 14A-14C show a virtual representation of the orthopedic system 300 positioned relative to a virtual representation of the femur 14 of a patient. These virtual representations can be achieved with scan data, CAD software, etc. as previously discussed. As previously discussed, the first arm 306 can be positioned to rest against the second saddle 27 of the neck 18 of the femur 14 as illustrated in FIGS. 14B and 14C. The second arm 308 can be aligned with the longitudinal axis L of the femur 14 as shown.

FIGS. 14A-14C additionally illustrate a virtual representation of the broach 50 as previously discussed in reference to FIGS. 5 and 6. As shown in FIGS. 14A-14C, the moveable portion 309 can be adjustable relative to the second saddle 27, the stationary portion 310, the assembly 302, etc. to indicate a depth of the proximal surface 320 of the broach 50. This depth can be a position of the proximal surface 320 of the broach 50 that is determined according to a pre-operative plan according to some examples.

As shown in FIGS. 14A-14C the virtual model can display a virtual rendering of the orthopedic system 300 can approximate the positioning of the assembly 302 (i.e. the first arm 306 on the second saddle 27) and the positioning of moveable portion 309 relative to the femur 14. The virtual model can also simulate positioning of the broach 50 and can determine a position of the moveable portion that approximates the proximal surface 320 of the broach 50. However, it is also contemplated that the orthopedic assembly 300 can be utilized without the aid of a pre-operative plan or virtual model, according to some examples.

Figure 15:
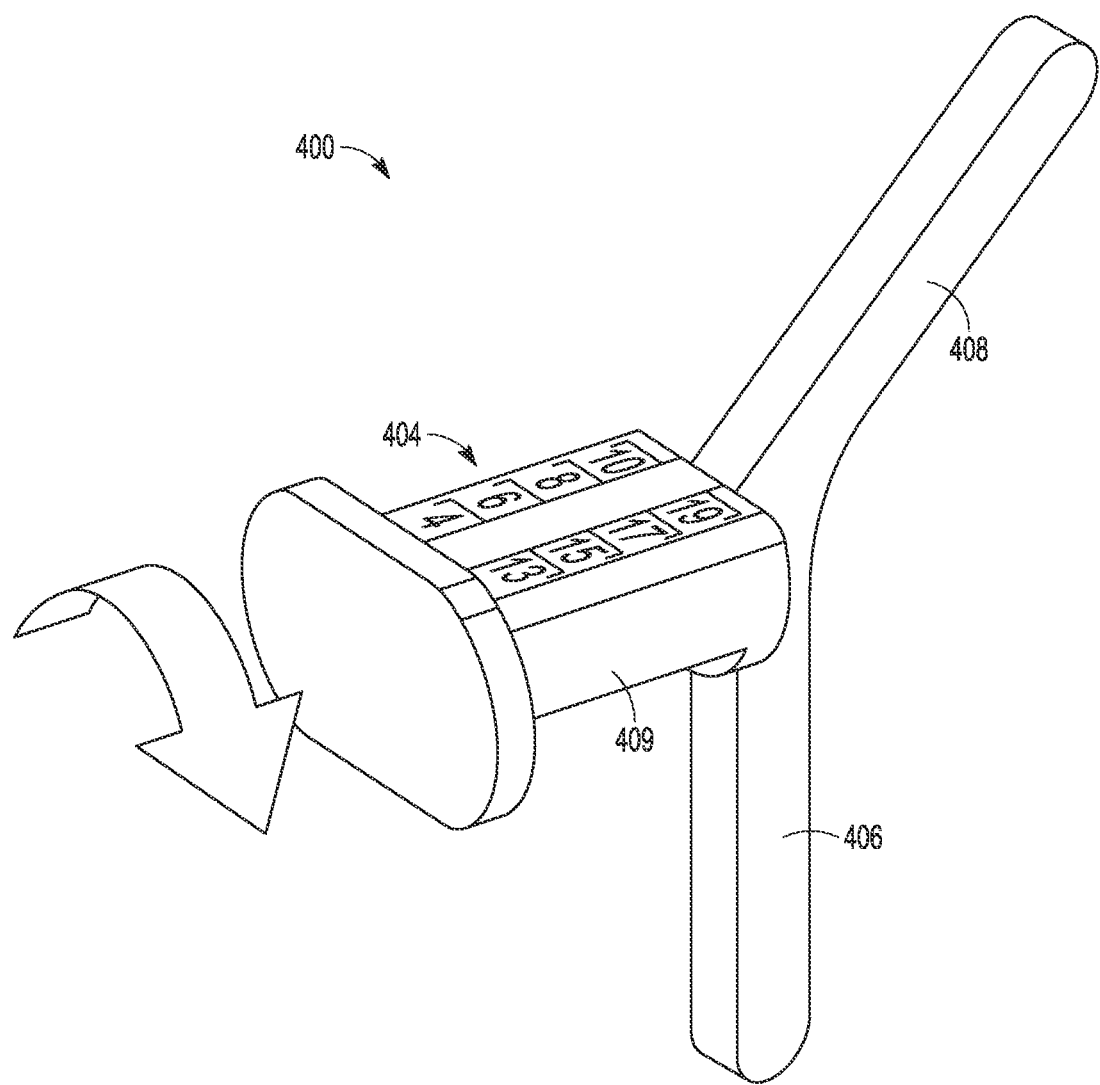
FIG. 15 is a perspective view of another embodiment of the second marking tool.

FIG. 15 shows an orthopedic system 400 of similar construction to that of the orthopedic system 300 including a first arm 406, second arm 408 and moveable portion 409. However, the orthopedic system 400 includes a modified body 404 with additional length to achieve further depth from the saddle of the neck of the femur for patient's having larger bone sizes or requiring a deeper broaching depth. As with the orthopedic system 300, the moveable portion 409 can be rotated or otherwise moved to achieve a desired position setting.

Figure 16:
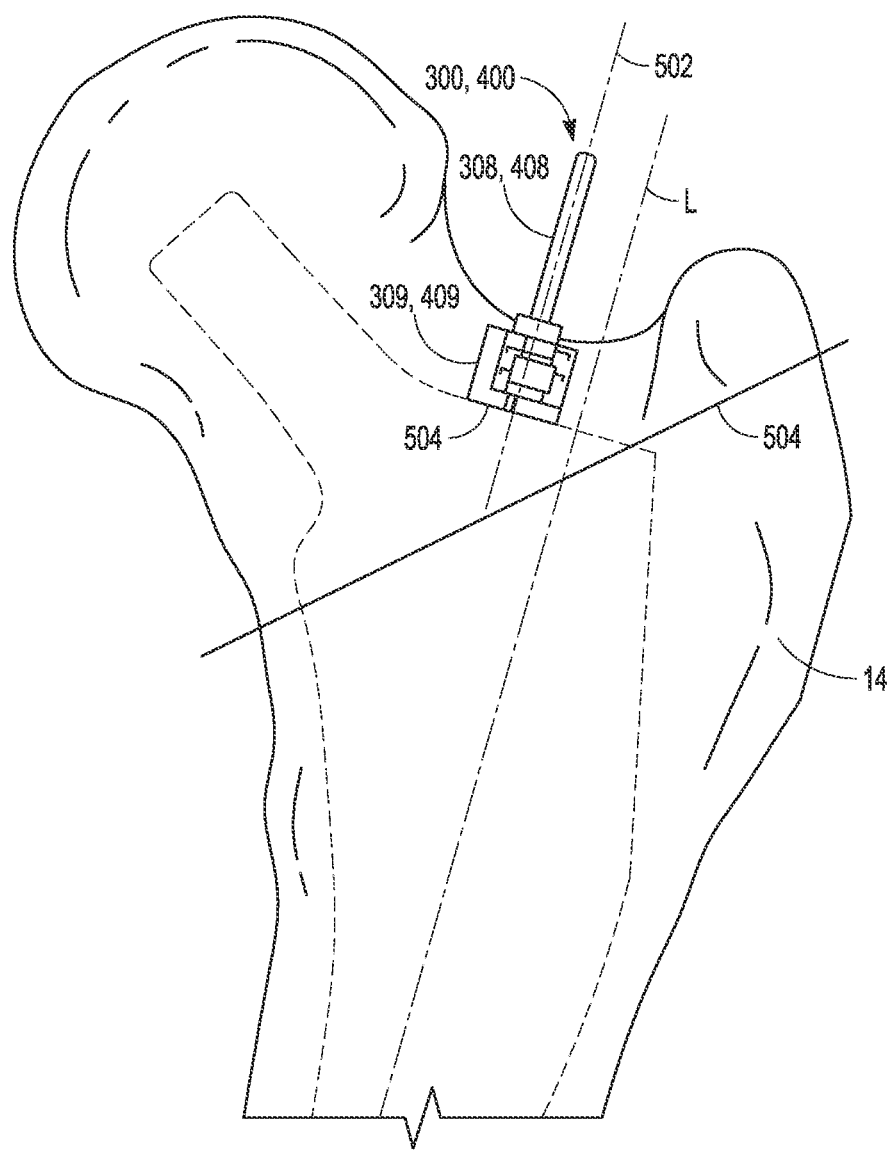
FIG. 16 illustrates a methodology with the second marking tool is seated on the proximal femur to identify a proximal surface where the broach would be located, in accordance with an example of the present disclosure.

FIG. 16 illustrates a methodology that can be utilized with the orthopedic system 300 or the orthopedic system 400. This methodology can include setting the movable portion 309, 409 to a desired height setting. The orthopedic system 300 or 400 can be placed with the first arm against the saddle. An axis 502 of the second arm 308, 408 can be aligned with the longitudinal axis L. The femur 14 can then be marked (indicated with dashed line 504) or resected using the distal end of the moveable portion 309, 409 of the orthopedic system 300, 400. A resection 504 can then be performed to remove the proximal end portion of the femur 14 using the marking 504 and additional criteria (such as those derived from the orthopedic systems 100 and 200) as previously discussed.

Figure 17:
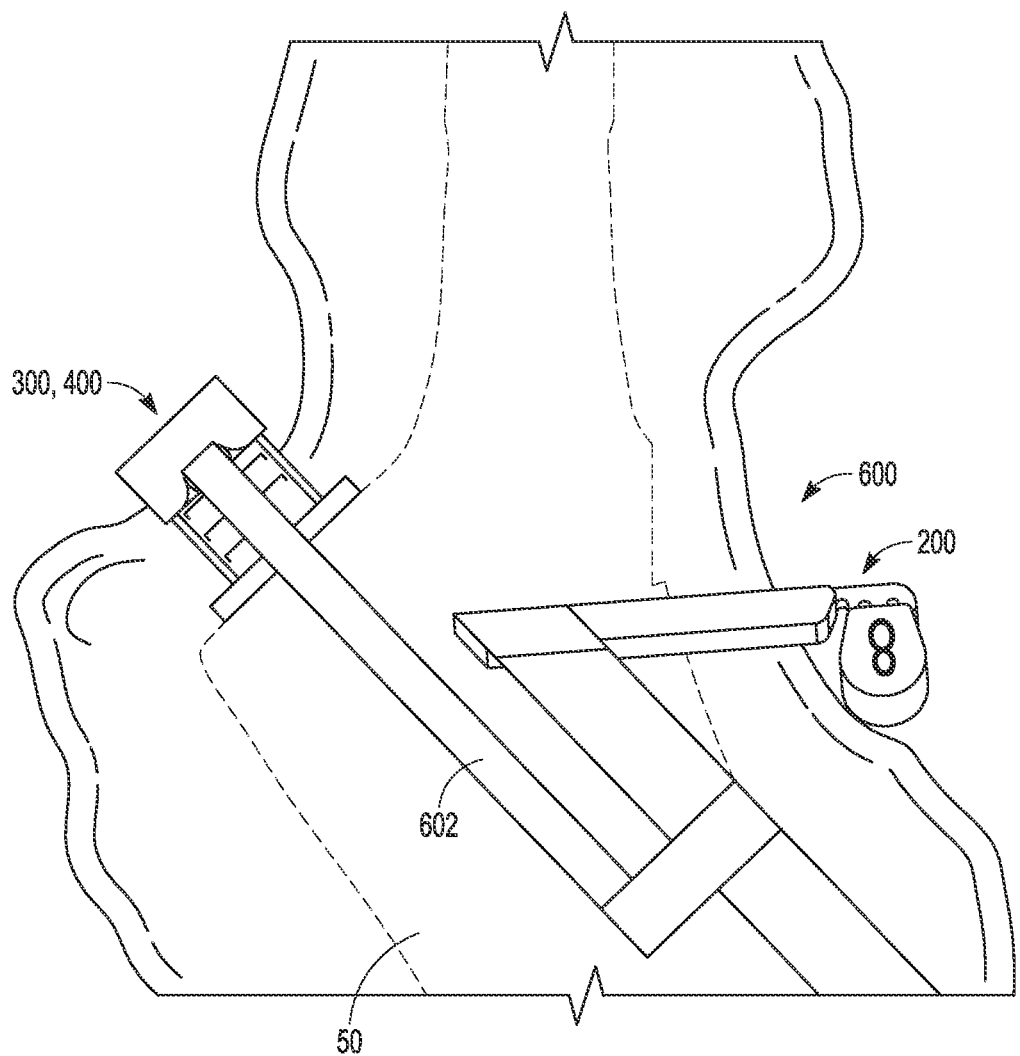
FIG. 17 is a perspective view of a third marking tool that includes features of the marking tool of FIGS. 8-11 and the second marking tool of FIGS. 12A-16, in accordance with an example of the present disclosure.

FIG. 17 shows an orthopedic system 600 that can combine the construction of the orthopedic systems 200, 300 and/or 400. The orthopedic system 600 thus can include the orthopedic system 200 with the shims and arm as previously discussed. The orthopedic system 600 further includes a modified second arm 602 of the orthopedic system 300 or 400. This second arm 602 can couple with the handle of the orthopedic system 200 as shown.

The orthopedic system 600 can be configured to make two markings on the femur 14. One marking can indicate the proximal surface of the broach 50 as discussed in reference to FIGS. 12A-16. The second marking can be made with the orthopedic system 200 (part of the orthopedic system 600) to indicate the resection line (i.e., "Resection Level" in FIG. 3, the resection 30, and the resection 504 as shown in other FIGURES herein).

ADDITIONAL NOTES

Certain examples are described herein as including logic or a number of components, modules, or mechanisms. Modules may constitute either software modules (e.g., code embodied on a machine-readable medium or in a transmission signal) or modules. A module is tangible unit capable of performing certain operations and may be configured or arranged in a certain manner. In examples, one or more computer systems (e.g., a standalone, client or server computer system) or one or more modules of a computer system (e.g., a processor or a group of processors) may be configured by software (e.g., an application or application portion) as a module that operates to perform certain operations as described herein.

In various examples, a module may be implemented mechanically or electronically. For example, a module may comprise dedicated circuitry or logic that is permanently configured (e.g., as a special-purpose processor, such as a field programmable gate array (FPGA) or an application-specific integrated circuit (ASIC)) to perform certain operations. A module may also comprise programmable logic or circuitry (e.g., as encompassed within a general-purpose processor or other programmable processor) that is temporarily configured by software to perform certain operations. It will be appreciated that the decision to implement a module mechanically, in dedicated and permanently configured circuitry, or in temporarily configured circuitry (e.g., configured by software) may be driven by cost and time considerations.

Accordingly, the term "module" can be understood to encompass a tangible entity, such as hardware, that can be that an entity that is physically constructed, permanently configured (e.g., hardwired) or temporarily configured (e.g., programmed) to operate in a certain manner and/or to perform certain operations described herein. Considering examples in which modules are temporarily configured (e.g., programmed), each of the modules need not be configured or instantiated at any one instance in time. For example, where the modules comprise a general-purpose processor configured using software, the general-purpose processor may be configured as respective different modules at different times. Software may accordingly configure a processor, for example, to constitute a particular module at one instance of time and to constitute a different module at a different instance of time.

Modules can provide information to, and receive information from, other modules. Accordingly, the described modules may be regarded as being communicatively coupled. Where multiple of such modules exist contemporaneously, communications may be achieved through signal transmission (e.g., over appropriate circuits and buses) that connect the modules. In examples in which multiple modules are configured or instantiated at different times, communications between such modules may be achieved, for example, through the storage and retrieval of information in memory structures to which the multiple modules have access. For example, one module may perform an operation, and store the output of that operation in a memory device to which it is communicatively coupled. A further module may then, at a later time, access the memory device to retrieve and process the stored output. Modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some examples, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example examples, the processor or processors may be located in a single location (e.g., within a home environment, an office environment or as a server farm), while in other examples the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Examples may be implemented in digital electronic circuitry, or in computer hardware, firmware, software, or in combinations of them. Examples may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In examples, operations may be performed by one or more programmable processors executing a computer program to perform functions by operating on input data and generating output. Method operations can also be performed by, and apparatus of examples may be implemented as, special purpose logic circuitry, e.g., a field programmable gate array (FPGA) or an application-specific integrated circuit (ASIC).

The computing system can include clients and servers. A client and server are generally remote from each other and typically interact through a communication network. The relationship of client and server arises by virtue of computer programs running on the respective computers and having a client-server relationship to each other. In examples deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various examples.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventor also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. An orthopedic device comprising:
   a body having a longitudinal extent with a first end opposing a second end, wherein the body is configured to extend across an end portion of a bone;
   a first portion configured to moveably couple to the first end of the body via a first two arms received in a first one or more slots, wherein the first two arms form a first linear track and the first portion includes a curved paddle configured to reference a first surface of the bone positioned to a first side of a longitudinal axis of the bone, wherein the curved paddle is coupled to an end of the first two arms; and
   a second portion configured to moveably couple to the second end of the body via a second two arms received in a second one or more slots, wherein the second two arms form a second linear track and the second portion includes a projection configured to reference a second surface of the bone positioned to a second side of the longitudinal axis of the bone;
   wherein the first portion with the curved paddle is configured to reference a proximal surface of a greater trochanter of a femur and the second portion with the projection is configured to reference a junction between a neck of the femur and a lesser trochanter of the femur.

2. The orthopedic device of claim 1, wherein the body has a surface for guiding a resection of the end portion of the bone.

3. The orthopedic device of claim 1, wherein the first linear track has a first plurality of teeth that engage mating teeth of a first actuator, and wherein the second linear track has a second plurality teeth that engage mating teeth of a second actuator.

4. The orthopedic device of claim 1, the body includes a first spring biased finger configured to engage a one of a linear arrangement of a first plurality of detents to lock the first portion in position relative to the body, and wherein the body includes a second spring biased finger configured to engage a second one of a linear arrangement of a second plurality of detents to lock the second portion in position relative to the body.

5. The orthopedic device of claim 1, wherein the body and the first portion each have first indicia, the first indicia indicative of a distance between the greater trochanter and the proximal surface of the body, and wherein the body and the second portion each have second indicia, the second indicia indicative of a distance between the junction between the neck of the femur and the lesser trochanter of the femur and the proximal surface of the body.

6. The orthopedic device of claim 1, wherein the projection is positioned lateral of the second two arms and the second linear track.

7. The orthopedic device of claim 1, further comprising:
   a first actuator positioned on a first lateral side of the body at the first end of the body; and
   a second actuator positioned on a second lateral side of the body at the second end of the body, wherein first actuator is offset from the second actuator across a longitudinal axis of the body.

8. An orthopedic system comprising:
   a body having a longitudinal extent with a first end opposing a second end, wherein the body is configured to extend across an end portion of a bone;
   a first portion configured to moveably couple to the first end of the body and configured to reference a first surface of the bone positioned to a first side of a longitudinal axis of the bone;
   a second portion configured to moveably couple to the second end of the body and configured to reference a second surface of the bone positioned to a second side of the longitudinal axis of the bone; and a computer including at least one processor and a memory device, the memory device including instructions that, when executed by the at least one processor, cause the computer to:
access image data of a target location including the bone of a patient, the image data including at least one of a bone size, a bone orientation and a bone shape;
display based upon the image data one or more patient-specific characteristics of bone;
determine one or more of a size, a shape and an orientation for an osteotomy of the end portion of the bone based at least in part upon the one or more patient-specific characteristics of the bone; and
convert the one or more patient-specific characteristics of anatomy of the patient to a first setting to position the first portion relative to the body and a second setting to position the second portion relative to the body.

9. The system of claim 8, further comprising instructions that cause the computer to construct a virtual model of the bone, wherein the virtual model displays a virtual rendering of the body, the first portion and the second portion and approximates the positioning the first portion, the body and the second portion relative to the bone along with the one or more patient-specific characteristics of the bone of the patient.

10. The system of claim 8, wherein the first setting and the second setting is one of a plurality of standard settings for the first portion and the second portion, and the first setting and the second setting is selected as a best match to the one or more patient-specific characteristics of the bone, and wherein the first portion, the second portion and the body have indicia corresponding to the plurality of standard settings, including first indicia indicative of a distance between a greater trochanter and a proximal surface of the body and second indicia indicative of a distance between a junction between a neck of a femur and a lesser trochanter of the femur and a proximal surface of the body.

11. An orthopedic device comprising:
a body having a longitudinal extent with a first end opposing a second end, wherein the body is configured to extend across an end portion of a bone;
a first portion configured to moveably couple to the first end of the body and configured to reference a first surface of the bone positioned to a first side of a longitudinal axis of the bone; and
a second portion configured to moveably couple to the second end of the body and configured to reference a second surface of the bone positioned to a second side of the longitudinal axis of the bone;
a first actuator positioned on a first lateral side of the body at the first end of the body; and
a second actuator positioned on a second lateral side of the body at the second end of the body, wherein the first actuator is offset from the second actuator across a longitudinal axis of the body;
wherein the body includes a first spring biased finger configured to engage a one of a linear arrangement of a first plurality of detents to lock the first portion in position relative to the body, and wherein the body includes a second spring biased finger configured to engage a second one of a linear arrangement of a second plurality of detents to lock the second portion in position relative to the body.

12. The orthopedic device of claim 11, wherein the first portion includes a first two arms received in a first one or more slots, wherein the first two arms form a first linear track and the first portion includes a curved paddle, wherein the curved paddle is coupled to an end of the first two arms, and wherein the curved paddle is configured to reference a proximal surface of a greater trochanter of a femur.

13. The orthopedic device of claim 12, wherein the second portion includes a second two arms received in a second one or more slots, wherein the second two arms form a second linear track and the second portion includes a projection, and wherein the projection is configured to reference a junction between a neck of the femur and a lesser trochanter of the femur.

14. The orthopedic device of claim 13, wherein the projection is positioned lateral of the second two arms and the second linear track.

15. The orthopedic device of claim 14, wherein the first linear track has a first plurality of teeth that engage mating teeth of the first actuator, and wherein the second linear track has a second plurality teeth that engage mating teeth of the second actuator.

16. The orthopedic device of claim 11, wherein the body has a surface for guiding a resection of the end portion of the bone.

17. The orthopedic device of claim 11, wherein the body and the first portion each have first indicia, the first indicia indicative of a distance between a greater trochanter of a femur and a proximal surface of the body, and wherein the body and the second portion each have second indicia, the second indicia indicative of a distance between a junction between a neck of the femur and a lesser trochanter of the femur and the proximal surface of the body.

* * * * *